United States Patent
Ofir et al.

(10) Patent No.: US 10,663,714 B2
(45) Date of Patent: May 26, 2020

(54) OPTICAL SYSTEM FOR AN ENDOSCOPE

(71) Applicant: EndoChoice, Inc., Alpharetta, GA (US)

(72) Inventors: Yaniv Ofir, Givat Haim Ihud (IL);
Robby Dascalo, Zichron Yaaqov (IL)

(73) Assignee: EndoChoice, Inc., Alpharetta, GA (US)

( * ) Notice: Subject to any disclaimer, the term of this patent is extended or adjusted under 35 U.S.C. 154(b) by 509 days.

(21) Appl. No.: 15/051,834

(22) Filed: Feb. 24, 2016

(65) Prior Publication Data

US 2016/0246048 A1     Aug. 25, 2016

Related U.S. Application Data

(60) Provisional application No. 62/120,141, filed on Feb. 24, 2015.

(51) Int. Cl.
| | | |
|---|---|---|
| *G02B 23/24* | (2006.01) | |
| *A61B 1/00* | (2006.01) | |
| *A61B 1/002* | (2006.01) | |

(52) U.S. Cl.
CPC ............ *G02B 23/243* (2013.01); *A61B 1/002* (2013.01); *A61B 1/0011* (2013.01); *A61B 1/00096* (2013.01)

(58) Field of Classification Search
None
See application file for complete search history.

(56) References Cited

U.S. PATENT DOCUMENTS

| | | | |
|---|---|---|---|
| 3,639,714 A | 2/1972 | Fujimoto | |
| 3,955,064 A | 5/1976 | Demetrio | |
| 4,027,697 A | 6/1977 | Bonney | |
| 4,037,588 A | 7/1977 | Heckele | |
| 4,084,401 A | 4/1978 | Belardi | |
| 4,402,313 A | 9/1983 | Yabe | |
| 4,461,282 A | 7/1984 | Ouchi | |
| 4,494,549 A | 1/1985 | Namba | |

(Continued)

FOREIGN PATENT DOCUMENTS

| | | |
|---|---|---|
| CA | 2297986 | 3/1999 |
| CA | 2765559 | 12/2010 |

(Continued)

OTHER PUBLICATIONS

International Search Report for PCT/US14/37004, dated Sep. 25, 2014.

(Continued)

*Primary Examiner* — Darryl J Collins
*Assistant Examiner* — Journey F Sumlar
(74) *Attorney, Agent, or Firm* — Bookoff McAndrews, PLLC

(57) ABSTRACT

A lens assembly of a viewing element for an endoscope has lenses and a barrel containing the lenses. The internal surface of the barrel is shaped in accordance with the relative position and size of the lenses and a lens holder encompassing at least a portion of the barrel. The barrel and/or the lens holder are injection-molded and can be variably positioned relative to each other. An optional adhesive layer that reduces or eliminates small particles from the viewing element is positioned on an inner surface of the barrel and/or lens holder and used to remove any internal particulate matter that may otherwise obstruct the field of view.

19 Claims, 8 Drawing Sheets

(56) References Cited

U.S. PATENT DOCUMENTS

| | | |
|---|---|---|
| 4,532,918 A | 8/1985 | Wheeler |
| 4,588,294 A | 5/1986 | Siegmund |
| 4,641,635 A | 2/1987 | Yabe |
| 4,727,859 A | 3/1988 | Lia |
| 4,764,001 A | 8/1988 | Yokota |
| 4,801,792 A | 1/1989 | Yamasita |
| 4,825,850 A | 5/1989 | Opie |
| 4,877,314 A | 10/1989 | Kanamori |
| 4,902,115 A | 2/1990 | Takahashi |
| 4,976,522 A | 12/1990 | Igarashi |
| 4,984,878 A | 1/1991 | Miyano |
| 5,007,406 A | 4/1991 | Takahashi |
| 5,014,685 A | 5/1991 | Takahashi |
| 5,193,525 A | 3/1993 | Silverstein |
| 5,224,929 A | 7/1993 | Remiszewski |
| 5,296,971 A | 3/1994 | Mori |
| 5,359,456 A | 10/1994 | Kikuchi |
| 5,395,329 A | 3/1995 | Fleischhacker |
| 5,447,148 A | 9/1995 | Oneda |
| 5,460,167 A | 10/1995 | Yabe |
| 5,464,007 A | 11/1995 | Krauter |
| 5,475,420 A | 12/1995 | Buchin |
| 5,489,256 A | 2/1996 | Adair |
| 5,518,501 A | 5/1996 | Oneda |
| 5,518,502 A | 5/1996 | Kaplan |
| 5,547,455 A | 8/1996 | McKenna |
| 5,547,457 A | 8/1996 | Tsuyuki |
| 5,575,755 A | 11/1996 | Krauter |
| 5,587,839 A | 12/1996 | Miyano |
| 5,630,782 A | 5/1997 | Adair |
| 5,630,798 A | 5/1997 | Beiser |
| 5,662,588 A | 9/1997 | Iida |
| 5,674,182 A | 10/1997 | Suzuki |
| 5,685,821 A | 11/1997 | Pike |
| 5,685,823 A | 11/1997 | Ito |
| 5,702,347 A | 12/1997 | Yabe |
| 5,707,344 A | 1/1998 | Nakazawa |
| 5,725,474 A | 3/1998 | Yasui |
| 5,725,476 A | 3/1998 | Yasui |
| 5,725,477 A | 3/1998 | Yasui |
| 5,725,478 A | 3/1998 | Saad |
| 5,777,797 A | 7/1998 | Miyano |
| 5,782,751 A | 7/1998 | Matsuno |
| 5,800,341 A | 9/1998 | McKenna |
| 5,810,715 A | 9/1998 | Moriyama |
| 5,810,717 A | 9/1998 | Maeda |
| 5,810,770 A | 9/1998 | Chin |
| 5,830,121 A | 11/1998 | Enomoto |
| 5,836,894 A | 11/1998 | Sarvazyan |
| 5,860,913 A | 1/1999 | Yamaya |
| 5,870,234 A | 2/1999 | EbbesmeierneeSchitthof |
| 5,916,148 A | 6/1999 | Tsuyuki |
| 5,940,126 A | 8/1999 | Kimura |
| 6,058,109 A | 5/2000 | Lechleider |
| 6,095,970 A | 8/2000 | Hidaka |
| 6,095,971 A | 8/2000 | Takahashi |
| 6,117,068 A | 9/2000 | Gourley |
| 6,181,481 B1 | 1/2001 | Yamamoto |
| 6,196,967 B1 | 3/2001 | Lim |
| 6,261,226 B1 | 7/2001 | McKenna |
| 6,277,064 B1 | 8/2001 | Yoon |
| 6,359,674 B1 | 3/2002 | Horiuchi |
| 6,375,610 B2 | 4/2002 | Verschuur |
| 6,402,738 B1 | 6/2002 | Ouchi |
| 6,419,626 B1 | 7/2002 | Yoon |
| 6,476,851 B1 | 11/2002 | Nakamura |
| 6,520,908 B1 | 2/2003 | Ikeda |
| 6,636,254 B1 | 10/2003 | Onishi |
| 6,638,214 B2 | 10/2003 | Akiba |
| 6,673,012 B2 | 1/2004 | Fujii |
| 6,690,337 B1 | 2/2004 | Mayer, III |
| 6,712,760 B2 | 3/2004 | Sano |
| 6,832,984 B2 | 12/2004 | Stelzer |
| 6,888,119 B2 | 5/2005 | Iizuka |
| 6,997,871 B2 | 2/2006 | Sonnenschein |
| 7,154,378 B1 | 12/2006 | Ertas |
| 7,435,218 B2 | 10/2008 | Krattiger |
| 7,621,869 B2 | 11/2009 | Ratnakar |
| 7,630,148 B1 | 12/2009 | Yang |
| 7,701,650 B2 | 4/2010 | Lin |
| 7,713,246 B2 | 5/2010 | Shia |
| 7,746,572 B2 | 6/2010 | Asami |
| 7,813,047 B2 | 10/2010 | Wang |
| 7,828,725 B2 | 11/2010 | Maruyama |
| 7,918,788 B2 | 4/2011 | Lin |
| 7,927,272 B2 | 4/2011 | Bayer |
| 7,967,745 B2 | 6/2011 | Gilad |
| 7,976,462 B2 | 7/2011 | Wright |
| 8,064,666 B2 | 11/2011 | Bayer |
| 8,182,422 B2 | 5/2012 | Bayer |
| 8,197,399 B2 | 6/2012 | Bayer |
| 8,235,887 B2 | 8/2012 | Bayer |
| 8,262,558 B2 | 9/2012 | Sato |
| 8,287,446 B2 | 10/2012 | Bayer |
| 8,289,381 B2 | 10/2012 | Bayer |
| 8,300,325 B2 | 10/2012 | Katahira |
| 8,310,530 B2 | 11/2012 | Bayer |
| 8,353,860 B2 | 1/2013 | Boulais |
| 8,447,132 B1 | 5/2013 | Galil |
| 8,449,457 B2 | 5/2013 | Aizenfeld |
| 8,460,182 B2 | 6/2013 | Ouyang |
| 8,585,584 B2 | 11/2013 | Ratnakar |
| 8,587,645 B2 | 11/2013 | Bayer |
| 8,672,836 B2 | 3/2014 | Higgins |
| 8,715,168 B2 | 5/2014 | Ratnakar |
| 8,797,392 B2 | 8/2014 | Bayer |
| 8,872,906 B2 | 10/2014 | Bayer |
| 8,899,761 B2 * | 12/2014 | Tonar ............ H01L 41/0973 359/511 |
| 8,926,502 B2 | 1/2015 | Levy |
| 9,044,185 B2 | 6/2015 | Bayer |
| 9,101,266 B2 | 8/2015 | Levi |
| 9,101,268 B2 | 8/2015 | Levy |
| 9,101,287 B2 | 8/2015 | Levy |
| 9,144,664 B2 | 9/2015 | Jacobsen |
| 9,158,103 B2 * | 10/2015 | Kato ............ A61B 1/00163 |
| 9,289,110 B2 | 3/2016 | Woolford |
| 9,314,147 B2 | 4/2016 | Levy |
| 9,320,419 B2 | 4/2016 | Kirma |
| 2001/0036322 A1 | 11/2001 | Bloomfield |
| 2002/0017515 A1 | 2/2002 | Obata |
| 2002/0047897 A1 | 4/2002 | Sugimoto |
| 2002/0087047 A1 | 7/2002 | Remijan |
| 2002/0109771 A1 | 8/2002 | Ledbetter |
| 2002/0109774 A1 | 8/2002 | Meron |
| 2002/0161279 A1 | 10/2002 | Luloh |
| 2002/0161281 A1 | 10/2002 | Jaffe |
| 2002/0172498 A1 | 11/2002 | Esenyan |
| 2002/0183591 A1 | 12/2002 | Matsuura |
| 2003/0030918 A1 | 2/2003 | Murayama |
| 2003/0063398 A1 | 4/2003 | Abe |
| 2003/0076411 A1 | 4/2003 | Iida |
| 2003/0083552 A1 | 5/2003 | Remijan |
| 2003/0128893 A1 | 7/2003 | Castorina |
| 2003/0139650 A1 | 7/2003 | Homma |
| 2003/0153897 A1 | 8/2003 | Russo |
| 2003/0158503 A1 | 8/2003 | Matsumoto |
| 2003/0163029 A1 | 8/2003 | Sonnenschein |
| 2004/0015054 A1 | 1/2004 | Hino |
| 2004/0046865 A1 | 3/2004 | Ueno |
| 2004/0061780 A1 | 4/2004 | Huffman |
| 2004/0064019 A1 | 4/2004 | Chang |
| 2004/0077927 A1 | 4/2004 | Ouchi |
| 2004/0106850 A1 | 6/2004 | Yamaya |
| 2004/0133072 A1 | 7/2004 | Kennedy |
| 2004/0138532 A1 | 7/2004 | Glukhovsky |
| 2004/0158129 A1 | 8/2004 | Okada |
| 2004/0160682 A1 | 8/2004 | Miyano |
| 2004/0190159 A1 | 9/2004 | Hasegawa |
| 2004/0249247 A1 | 12/2004 | Iddan |
| 2004/0260151 A1 | 12/2004 | Akiba |
| 2005/0018042 A1 | 1/2005 | Rovegno |
| 2005/0020876 A1 | 1/2005 | Shioda |
| 2005/0038317 A1 | 2/2005 | Ratnakar |

(56) References Cited

U.S. PATENT DOCUMENTS

| | | |
|---|---|---|
| 2005/0047134 A1 | 3/2005 | Mueller |
| 2005/0057687 A1 | 3/2005 | Irani |
| 2005/0090709 A1 | 4/2005 | Okada |
| 2005/0096501 A1 | 5/2005 | Stelzer |
| 2005/0119527 A1 | 6/2005 | Banik |
| 2005/0124858 A1 | 6/2005 | Matsuzawa |
| 2005/0222499 A1 | 10/2005 | Banik |
| 2005/0234296 A1 | 10/2005 | Saadat |
| 2005/0234347 A1 | 10/2005 | Yamataka |
| 2005/0251127 A1 | 11/2005 | Brosch |
| 2005/0272975 A1 | 12/2005 | McWeeney |
| 2005/0277808 A1 | 12/2005 | Sonnenschein |
| 2005/0283048 A1 | 12/2005 | Gill |
| 2006/0004257 A1 | 1/2006 | Gilad |
| 2006/0047184 A1 | 3/2006 | Banik |
| 2006/0063976 A1 | 3/2006 | Aizenfeld |
| 2006/0069314 A1 | 3/2006 | Farr |
| 2006/0111613 A1 | 5/2006 | Boutillette |
| 2006/0114986 A1 | 6/2006 | Knapp |
| 2006/0149129 A1 | 7/2006 | Watts |
| 2006/0171693 A1 | 8/2006 | Todd |
| 2006/0173245 A1 | 8/2006 | Todd |
| 2006/0183975 A1 | 8/2006 | Saadat |
| 2006/0184037 A1 | 8/2006 | Ince |
| 2006/0189845 A1 | 8/2006 | Maahs |
| 2006/0215406 A1 | 9/2006 | Thrailkill |
| 2006/0235306 A1 | 10/2006 | Cotter |
| 2006/0252994 A1 | 11/2006 | Ratnakar |
| 2006/0264704 A1 | 11/2006 | Fujimori |
| 2006/0290802 A1* | 12/2006 | Webster ............... H04N 5/2253 348/340 |
| 2006/0293556 A1 | 12/2006 | Garner |
| 2007/0015989 A1 | 1/2007 | Desai |
| 2007/0049803 A1 | 3/2007 | Moriyama |
| 2007/0055100 A1 | 3/2007 | Kato |
| 2007/0079029 A1 | 4/2007 | Carlson |
| 2007/0088193 A1 | 4/2007 | Omori |
| 2007/0100206 A1 | 5/2007 | Lin |
| 2007/0106119 A1 | 5/2007 | Hirata |
| 2007/0118015 A1 | 5/2007 | Wendlandt |
| 2007/0142711 A1 | 6/2007 | Bayer |
| 2007/0162095 A1 | 7/2007 | Kimmel |
| 2007/0167681 A1 | 7/2007 | Gill |
| 2007/0177008 A1 | 8/2007 | Bayer |
| 2007/0177009 A1 | 8/2007 | Bayer |
| 2007/0185384 A1 | 8/2007 | Bayer |
| 2007/0188427 A1 | 8/2007 | Lys |
| 2007/0197875 A1 | 8/2007 | Osaka |
| 2007/0203396 A1 | 8/2007 | McCutcheon |
| 2007/0206945 A1 | 9/2007 | Delorme |
| 2007/0213591 A1 | 9/2007 | Aizenfeld |
| 2007/0229656 A1 | 10/2007 | Khait |
| 2007/0241895 A1 | 10/2007 | Morgan |
| 2007/0244353 A1 | 10/2007 | Larsen |
| 2007/0244354 A1 | 10/2007 | Bayer |
| 2007/0247867 A1 | 10/2007 | Hunter |
| 2007/0249907 A1 | 10/2007 | Boulais |
| 2007/0265492 A1 | 11/2007 | Sonnenschein |
| 2007/0270642 A1 | 11/2007 | Bayer |
| 2007/0279486 A1 | 12/2007 | Bayer |
| 2007/0286764 A1 | 12/2007 | Noguchi |
| 2007/0293720 A1 | 12/2007 | Bayer |
| 2008/0009673 A1 | 1/2008 | Khachi |
| 2008/0021274 A1 | 1/2008 | Bayer |
| 2008/0025413 A1 | 1/2008 | Apostolopoulos |
| 2008/0036864 A1 | 2/2008 | McCubbrey |
| 2008/0045797 A1 | 2/2008 | Yasushi |
| 2008/0058601 A1 | 3/2008 | Fujimori |
| 2008/0071290 A1 | 3/2008 | Larkin |
| 2008/0091065 A1 | 4/2008 | Oshima |
| 2008/0130108 A1 | 6/2008 | Bayer |
| 2008/0151070 A1 | 6/2008 | Shiozawa |
| 2008/0161646 A1 | 7/2008 | Gomez |
| 2008/0163652 A1 | 7/2008 | Shatskin |
| 2008/0167529 A1 | 7/2008 | Otawara |
| 2008/0177139 A1 | 7/2008 | Courtney |
| 2008/0183034 A1 | 7/2008 | Henkin |
| 2008/0183043 A1 | 7/2008 | Spinnler |
| 2008/0221388 A1 | 7/2008 | Courtney |
| 2008/0246771 A1 | 10/2008 | ONeal |
| 2008/0253686 A1 | 10/2008 | Bayer |
| 2008/0262312 A1 | 10/2008 | Carroll |
| 2008/0275298 A1 | 11/2008 | Ratnakar |
| 2008/0303898 A1 | 12/2008 | Nishimura |
| 2009/0005643 A1 | 1/2009 | Smith |
| 2009/0023998 A1 | 1/2009 | Ratnakar |
| 2009/0030275 A1 | 1/2009 | Nicolaou |
| 2009/0054790 A1 | 2/2009 | Czaniera |
| 2009/0062615 A1 | 3/2009 | Yamaya |
| 2009/0076327 A1 | 3/2009 | Ohki |
| 2009/0082624 A1 | 3/2009 | Joko |
| 2009/0086017 A1 | 4/2009 | Miyano |
| 2009/0135245 A1 | 5/2009 | Luo |
| 2009/0137875 A1 | 5/2009 | Kitagawa |
| 2009/0143647 A1 | 6/2009 | Banju |
| 2009/0147076 A1 | 6/2009 | Ertas |
| 2009/0182917 A1 | 7/2009 | Kim |
| 2009/0213211 A1 | 8/2009 | Bayer |
| 2009/0216084 A1 | 8/2009 | Yamane |
| 2009/0225159 A1 | 9/2009 | Schneider |
| 2009/0231419 A1 | 9/2009 | Bayer |
| 2009/0234183 A1 | 9/2009 | Abe |
| 2009/0253966 A1 | 10/2009 | Ichimura |
| 2009/0287188 A1 | 11/2009 | Golden |
| 2009/0287192 A1 | 11/2009 | Vivenzio |
| 2009/0299144 A1 | 12/2009 | Shigemori |
| 2010/0010309 A1 | 1/2010 | Kitagawa |
| 2010/0016673 A1 | 1/2010 | Bandy |
| 2010/0053312 A1 | 3/2010 | Watanabe |
| 2010/0069713 A1 | 3/2010 | Endo |
| 2010/0073470 A1 | 3/2010 | Takasaki |
| 2010/0073948 A1 | 3/2010 | Stein |
| 2010/0076268 A1 | 3/2010 | Takasugi |
| 2010/0123950 A1 | 5/2010 | Fujiwara |
| 2010/0130822 A1 | 5/2010 | Katayama |
| 2010/0141763 A1 | 6/2010 | Itoh |
| 2010/0160729 A1 | 6/2010 | Smith |
| 2010/0174144 A1 | 7/2010 | Hsu |
| 2010/0231702 A1 | 9/2010 | Tsujimura |
| 2010/0245653 A1 | 9/2010 | Bodor |
| 2010/0249513 A1 | 9/2010 | Tydlaska |
| 2010/0280322 A1 | 11/2010 | Mizuyoshi |
| 2010/0296178 A1 | 11/2010 | Genet |
| 2010/0326703 A1 | 12/2010 | Gilad |
| 2011/0004058 A1 | 1/2011 | Oneda |
| 2011/0004059 A1 | 1/2011 | Arneson |
| 2011/0034769 A1 | 2/2011 | Adair |
| 2011/0063427 A1 | 3/2011 | Fengler |
| 2011/0084835 A1 | 4/2011 | Whitehouse |
| 2011/0140003 A1 | 6/2011 | Beck |
| 2011/0160530 A1 | 6/2011 | Ratnakar |
| 2011/0160535 A1 | 6/2011 | Bayer |
| 2011/0169931 A1 | 7/2011 | Pascal |
| 2011/0184243 A1 | 7/2011 | Wright |
| 2011/0211267 A1 | 9/2011 | Takato |
| 2011/0254937 A1 | 10/2011 | Yoshino |
| 2011/0263938 A1 | 10/2011 | Levy |
| 2011/0282144 A1 | 11/2011 | Gettman |
| 2011/0292258 A1 | 12/2011 | Adler |
| 2012/0040305 A1 | 2/2012 | Karazivan |
| 2012/0050606 A1 | 3/2012 | Debevec |
| 2012/0053407 A1 | 3/2012 | Levy |
| 2012/0057251 A1 | 3/2012 | Takato |
| 2012/0065468 A1 | 3/2012 | Levy |
| 2012/0076425 A1 | 3/2012 | Brandt |
| 2012/0162402 A1 | 6/2012 | Amano |
| 2012/0200683 A1 | 8/2012 | Oshima |
| 2012/0209071 A1 | 8/2012 | Bayer |
| 2012/0209289 A1 | 8/2012 | Duque |
| 2012/0212630 A1 | 8/2012 | Pryor |
| 2012/0220832 A1 | 8/2012 | Nakade |
| 2012/0224026 A1 | 9/2012 | Bayer |
| 2012/0229615 A1 | 9/2012 | Kirma |
| 2012/0232340 A1 | 9/2012 | Levy |

(56) References Cited

U.S. PATENT DOCUMENTS

| | | |
|---|---|---|
| 2012/0232343 A1 | 9/2012 | Levy |
| 2012/0253121 A1 | 10/2012 | Kitano |
| 2012/0277535 A1 | 11/2012 | Hoshino |
| 2012/0281536 A1 | 11/2012 | Gell |
| 2012/0289858 A1 | 11/2012 | Ouyang |
| 2012/0300999 A1 | 11/2012 | Bayer |
| 2013/0053646 A1 | 2/2013 | Yamamoto |
| 2013/0057724 A1 | 3/2013 | Miyahara |
| 2013/0060086 A1 | 3/2013 | Talbert |
| 2013/0066297 A1 | 3/2013 | Shtul |
| 2013/0077257 A1 | 3/2013 | Tsai |
| 2013/0085329 A1 | 4/2013 | Morrissette |
| 2013/0109916 A1 | 5/2013 | Levy |
| 2013/0116506 A1 | 5/2013 | Bayer |
| 2013/0131447 A1 | 5/2013 | Benning |
| 2013/0137930 A1 | 5/2013 | Menabde |
| 2013/0141557 A1 | 6/2013 | Kawata |
| 2013/0150671 A1 | 6/2013 | Levy |
| 2013/0158344 A1 | 6/2013 | Taniguchi |
| 2013/0169843 A1 | 7/2013 | Ono |
| 2013/0172670 A1 | 7/2013 | Levy |
| 2013/0172676 A1 | 7/2013 | Levy |
| 2013/0197309 A1 | 8/2013 | Sakata |
| 2013/0197556 A1 | 8/2013 | Shelton |
| 2013/0222640 A1 | 8/2013 | Baek |
| 2013/0253268 A1 | 9/2013 | Okada |
| 2013/0264465 A1 | 10/2013 | Dai |
| 2013/0267778 A1 | 10/2013 | Rehe |
| 2013/0271588 A1 | 10/2013 | Kirma |
| 2013/0274551 A1 | 10/2013 | Kirma |
| 2013/0281925 A1 | 10/2013 | Benscoter |
| 2013/0296649 A1* | 11/2013 | Kirma ............... A61B 1/00177 600/109 |
| 2013/0303979 A1 | 11/2013 | Stieglitz |
| 2013/0317295 A1 | 11/2013 | Morse |
| 2014/0018624 A1 | 1/2014 | Bayer |
| 2014/0031627 A1 | 1/2014 | Jacobs |
| 2014/0046136 A1 | 2/2014 | Bayer |
| 2014/0107418 A1 | 4/2014 | Ratnakar |
| 2014/0148644 A1 | 5/2014 | Levi |
| 2014/0184766 A1 | 7/2014 | Amling |
| 2014/0213850 A1 | 7/2014 | Levy |
| 2014/0225998 A1 | 8/2014 | Dai |
| 2014/0276207 A1 | 9/2014 | Ouyang |
| 2014/0296628 A1 | 10/2014 | Kirma |
| 2014/0296643 A1 | 10/2014 | Levy |
| 2014/0296866 A1 | 10/2014 | Salman |
| 2014/0298932 A1 | 10/2014 | Okamoto |
| 2014/0309495 A1 | 10/2014 | Kirma |
| 2014/0316198 A1 | 10/2014 | Krivopisk |
| 2014/0316204 A1 | 10/2014 | Ofir |
| 2014/0320617 A1 | 10/2014 | Parks |
| 2014/0333742 A1 | 11/2014 | Salman |
| 2014/0333743 A1 | 11/2014 | Gilreath |
| 2014/0336459 A1 | 11/2014 | Bayer |
| 2014/0343358 A1 | 11/2014 | Hameed |
| 2014/0343361 A1 | 11/2014 | Salman |
| 2014/0343489 A1 | 11/2014 | Lang |
| 2014/0364691 A1 | 12/2014 | Krivopisk |
| 2014/0364692 A1 | 12/2014 | Salman |
| 2014/0364694 A1 | 12/2014 | Avron |
| 2015/0005581 A1 | 1/2015 | Salman |
| 2015/0045614 A1 | 2/2015 | Krivopisk |
| 2015/0057500 A1 | 2/2015 | Salman |
| 2015/0094536 A1 | 4/2015 | Wieth |
| 2015/0099925 A1 | 4/2015 | Davidson |
| 2015/0099926 A1 | 4/2015 | Davidson |
| 2015/0105618 A1 | 4/2015 | Levy |
| 2015/0164308 A1 | 6/2015 | Ratnakar |
| 2015/0182105 A1 | 7/2015 | Salman |
| 2015/0196190 A1 | 7/2015 | Levy |
| 2015/0201827 A1 | 7/2015 | Sidar |
| 2015/0208900 A1 | 7/2015 | Vidas |
| 2015/0208909 A1 | 7/2015 | Davidson |
| 2015/0223676 A1 | 8/2015 | Bayer |
| 2015/0230698 A1 | 8/2015 | Cline |
| 2015/0305601 A1 | 10/2015 | Levi |
| 2015/0313445 A1 | 11/2015 | Davidson |
| 2015/0313450 A1 | 11/2015 | Wieth |
| 2015/0313451 A1 | 11/2015 | Salman |
| 2015/0320300 A1 | 11/2015 | Gershov |
| 2015/0342446 A1 | 12/2015 | Levy |
| 2015/0359415 A1 | 12/2015 | Lang |
| 2015/0374206 A1 | 12/2015 | Shimony |
| 2016/0015257 A1 | 1/2016 | Levy |
| 2016/0015258 A1 | 1/2016 | Levin |
| 2016/0058268 A1 | 3/2016 | Salman |
| 2016/0197595 A1* | 7/2016 | Obata ............... H03H 9/1021 331/158 |

FOREIGN PATENT DOCUMENTS

| | | |
|---|---|---|
| CA | 2812097 | 3/2012 |
| CA | 2798716 | 6/2013 |
| CA | 2798729 | 6/2013 |
| CN | 103348470 | 10/2013 |
| CN | 103403605 | 11/2013 |
| CN | 103491854 | 1/2014 |
| CN | 103702604 | 4/2014 |
| CN | 103732120 | 4/2014 |
| CN | 104717916 | 6/2015 |
| CN | 105246393 | 1/2016 |
| CN | 105324065 | 2/2016 |
| CN | 105324066 | 2/2016 |
| CN | 105338875 | 2/2016 |
| CN | 105358042 | 2/2016 |
| CN | 105358043 | 2/2016 |
| CN | 105377106 | 3/2016 |
| CN | 105407788 | 3/2016 |
| DE | 202010016900 | 5/2011 |
| EP | 1690497 | 8/2006 |
| EP | 1835844 | 9/2007 |
| EP | 1968425 | 9/2008 |
| EP | 1986541 | 11/2008 |
| EP | 1988813 | 11/2008 |
| EP | 2023794 | 2/2009 |
| EP | 2023795 | 2/2009 |
| EP | 2190341 | 6/2010 |
| EP | 2211683 | 8/2010 |
| EP | 2457492 | 5/2012 |
| EP | 2457493 | 5/2012 |
| EP | 1988812 | 11/2012 |
| EP | 2520218 | 11/2012 |
| EP | 2604175 | 6/2013 |
| EP | 2618718 | 7/2013 |
| EP | 2635932 | 9/2013 |
| EP | 2648602 | 10/2013 |
| EP | 2649648 | 10/2013 |
| EP | 2672878 | 12/2013 |
| EP | 2736400 | 6/2014 |
| EP | 2744390 | 6/2014 |
| EP | 2442706 | 11/2014 |
| EP | 2865322 | 4/2015 |
| EP | 2908714 | 8/2015 |
| EP | 2979123 | 2/2016 |
| EP | 2991537 | 3/2016 |
| EP | 2994032 | 3/2016 |
| EP | 2994033 | 3/2016 |
| EP | 2994034 | 3/2016 |
| EP | 2996536 | 3/2016 |
| EP | 2996541 | 3/2016 |
| EP | 2996542 | 3/2016 |
| EP | 2996621 | 3/2016 |
| GB | 12196628 | 3/2015 |
| JP | H1043129 | 2/1998 |
| JP | H10239740 | 9/1998 |
| JP | 11137512 | 5/1999 |
| JP | 2005253543 | 9/2005 |
| JP | 2006025888 | 2/2006 |
| JP | 2006068109 | 3/2006 |
| JP | 2010178766 A | 8/2010 |
| JP | 2012135432 | 7/2012 |
| JP | 2013116277 A2 | 6/2013 |
| JP | 2013123647 | 6/2013 |

(56) References Cited

FOREIGN PATENT DOCUMENTS

| | | |
|---|---|---|
| JP | 2013123648 | 6/2013 |
| JP | 2013208459 | 10/2013 |
| JP | 2013215582 | 10/2013 |
| JP | 2013230383 | 11/2013 |
| JP | 2013542467 | 11/2013 |
| JP | 2013544617 | 12/2013 |
| JP | 2014524303 | 9/2014 |
| JP | 2014524819 | 9/2014 |
| JP | 2015533300 | 11/2015 |
| WO | 2006073676 | 7/2006 |
| WO | 2006073725 | 7/2006 |
| WO | 2007070644 | 6/2007 |
| WO | 2007092533 | 8/2007 |
| WO | 2007092636 | 8/2007 |
| WO | 2007087421 | 11/2007 |
| WO | 2007136859 | 11/2007 |
| WO | 2007136879 | 11/2007 |
| WO | 2008015164 | 2/2008 |
| WO | 2009014895 | 1/2009 |
| WO | 2009015396 | 1/2009 |
| WO | 2009049322 | 4/2009 |
| WO | 2009049324 | 4/2009 |
| WO | 2009062179 | 5/2009 |
| WO | 2010146587 | 12/2010 |
| WO | 2012038958 | 3/2012 |
| WO | 2012056453 | 5/2012 |
| WO | 2012075153 A2 | 6/2012 |
| WO | 2012077116 | 6/2012 |
| WO | 2012077117 | 6/2012 |
| WO | 2012096102 | 7/2012 |
| WO | 2012120507 | 9/2012 |
| WO | 2013014673 | 1/2013 |
| WO | 2013024476 | 2/2013 |
| WO | 2014061023 | 4/2014 |
| WO | 2014160983 | 10/2014 |
| WO | 2014179236 | 11/2014 |
| WO | 2014182723 | 11/2014 |
| WO | 2014182728 | 11/2014 |
| WO | 2014183012 | 11/2014 |
| WO | 2014186230 | 11/2014 |
| WO | 2014186519 | 11/2014 |
| WO | 2014186521 | 11/2014 |
| WO | 2014186525 | 11/2014 |
| WO | 2014186775 | 11/2014 |
| WO | 2014210516 | 12/2014 |
| WO | 2015002847 | 1/2015 |
| WO | 2015047631 | 4/2015 |
| WO | 2015050829 | 4/2015 |
| WO | 2015084442 | 6/2015 |
| WO | 2015095481 | 6/2015 |
| WO | 2015112747 | 7/2015 |
| WO | 2015112899 | 7/2015 |
| WO | 2015134060 | 9/2015 |
| WO | 2015168066 | 11/2015 |
| WO | 2015168664 | 11/2015 |
| WO | 2015171732 | 11/2015 |
| WO | 2015175246 | 11/2015 |
| WO | 2016014581 | 1/2016 |
| WO | 2016033403 | 3/2016 |

OTHER PUBLICATIONS

International Search Report for PCT/US2014/037526, dated Oct. 16, 2014.
International Search Report for PCT/US14/38094, dated Nov. 6, 2014.
International Search Report for PCT/US2015/012751, dated Jun. 26, 2015.
International Search Report for PCT/US2014/58143, dated Jan. 21, 2015.
International Search Report for PCT/US2014/071085, dated Mar. 27, 2015.
International Search Report for PCT/US2015/027902, dated Jul. 23, 2015.
International Search Report for PCT/US2015/012506, dated Dec. 11, 2015.
International Search Report for PCT/US2015/29421, dated Aug. 7, 2015.
International Search Report for PCT/US2015/28962, dated Jul. 28, 2015.
International Search Report for PCT/US2015/47334, dated Dec. 28, 2015.
International Search Report for PCT/US2015/41396, dated Sep. 29, 2015.
International Search Report for PCT/US2015/66486, dated Dec. 17, 2015.
International Search Report for PCT/US2015/6548, dated Feb. 26, 2016.
Office Action dated Feb. 26, 2016 for U.S. Appl. No. 14/274,323.
Office Action dated Feb. 4, 2016 for U.S. Appl. No. 14/271,234.
Corrected Notice of Allowance dated Apr. 13, 2016 for U.S. Appl. No. 13/680,646.
Notice of Allowance dated Mar. 28, 2016 for U.S. Appl. No. 13/413,059.
Notice of Allowance dated Mar. 29, 2016 for U.S. Appl. No. 13/680,646.
Office Action dated Mar. 23, 2016 for U.S. Appl. No. 13/713,449.
Office Action dated Mar. 24, 2016 for U.S. Appl. No. 13/212,627.
Office Action dated Mar. 28, 2016 for U.S. Appl. No. 13/119,032.
Office Action dated May 25, 2016 for U.S. Appl. No. 14/271,234.
Office Action dated May 5, 2016 for U.S. Appl. No. 14/278,338.
Office Action dated May 6, 2016 for U.S. Appl. No. 14/263,896.
Office Action dated Jun. 30, 2016 for U.S. Appl. No. 13/655,120.
Office Action dated Jun. 28, 2016 for U.S. Appl. No. 14/278,293.
Office Action dated Jul. 1, 2016 for U.S. Appl. No. 14/229,699.
Office Action dated Jul. 15, 2016 for U.S. Appl. No. 14/273,923.
Notice of Allowance dated Jul. 15, 2016 for U.S. Appl. No. 14/274,323.
Office Action dated Jul. 22, 2016 for U.S. Appl. No. 14/549,265.
Sherman L.M., Plastics That Conduct Hear, Plastics Technology, Jun. 2001—article obtained online from http://www.ptonline.com/articles/plastics-that-conduct-heat.
Office Action dated Aug. 11, 2016 for U.S. Appl. No. 14/318,249.
Office Action dated Apr. 28, 2016 for U.S. Appl. No. 13/992,014.
Notice of Allowance dated Aug. 26, 2016 for U.S. Appl. No. 13/212,627.
Office Action dated Sep. 2, 2016 for U.S. Appl. No. 14/278,338.
Office Action dated Sep. 16, 2016 for U.S. Appl. No. 13/992,014.
Notice of Allowance dated Oct. 12, 2016 for U.S. Appl. No. 13/119,032.
Office Action dated Oct. 7, 2016 for U.S. Appl. No. 13/713,449.
Office Action dated Oct. 5, 2016 for U.S. Appl. No. 14/271,270.
Notice of Allowance dated Oct. 13, 2016 for U.S. Appl. No. 14/273,923.
Notice of Allowance dated Nov. 9, 2016 for U.S. Appl. No. 13/557,114.
Office Action dated Dec. 1, 2016 for U.S. Appl. No. 14/278,293.
Office Action dated Dec. 9, 2016 for U.S. Appl. No. 14/549,265.
Office Action dated Dec. 16, 2016 for U.S. Appl. No. 14/263,896.
Notice of Allowance dated Dec. 28, 2016 for U.S. Appl. No. 14/229,699.
Notice of Allowance dated Dec. 27, 2016 for U.S. Appl. No. 14/317,863.
Office Action dated Dec. 27, 2016 for U.S. Appl. No. 14/603,137.
Office Action dated Dec. 29, 2016 for U.S. Appl. No. 15/077,513.
Office Action dated Dec. 30, 2016 for U.S. Appl. No. 14/457,268.
Office Action dated Jan. 17, 2017 for U.S. Appl. No. 14/318,189.
Notice of Allowance dated Jan. 31, 2017 for U.S. Appl. No. 14/271,234.
Office Action dated Feb. 2, 2017 for U.S. Appl. No. 14/278,338.
Office Action dated Feb. 9, 2017 for U.S. Appl. No. 14/746,986.
Office Action dated Feb. 6, 2017 for U.S. Appl. No. 14/751,835.
Office Action dated Feb. 14, 2017 for U.S. Appl. No. 14/271,270.
Office Action dated Feb. 23, 2017 for U.S. Appl. No. 14/318,249.
Office Action dated Mar. 9, 2017 for U.S. Appl. No. 14/791,316.
Office Action dated Mar. 21, 2017 for U.S. Appl. No. 13/992,014.
Office Action dated Mar. 20, 2017 for U.S. Appl. No. 14/278,293.

(56) References Cited

OTHER PUBLICATIONS

Notice of Allowance dated Mar. 21, 2017 for U.S. Appl. No. 14/549,265.
Office Action dated Mar. 22, 2017 for U.S. Appl. No. 14/705,355.
Office Action dated Mar. 24, 2017 for U.S. Appl. No. 14/838,509.
Notice of Allowance dated Apr. 12, 2017 for U.S. Appl. No. 14/603,137.
Notice of Allowance dated Apr. 18, 2017 for U.S. Appl. No. 13/713,449.
Office Action dated Apr. 19, 2017 for U.S. Appl. No. 14/988,551.
Notice of Allowability dated Apr. 21, 2017 for U.S. Appl. No. 14/549,265.
Office Action dated May 11, 2017 for U.S. Appl. No. 14/278,293.
Office Action dated May 10, 2017 for U.S. Appl. No. 14/988,551.
Office Action dated May 5, 2017 for U.S. Appl. No. 15/077,513.
Notice of Allowance dated May 15, 2017 for U.S. Appl. No. 14/271,270.
Office Action dated May 15, 2017 for U.S. Appl. No. 14/278,293.
Office Action dated May 18, 2017 for U.S. Appl. No. 14/278,338.
Notice of Allowance dated May 16, 2017 for U.S. Appl. No. 14/746,986.
Notice of Allowance dated May 23, 2017 for U.S. Appl. No. 13/655,120.
Notice of Allowance dated May 25, 2017 for U.S. Appl. No. 14/318,189.
Office Action dated May 23, 2017 for U.S. Appl. No. 14/500,975.

* cited by examiner

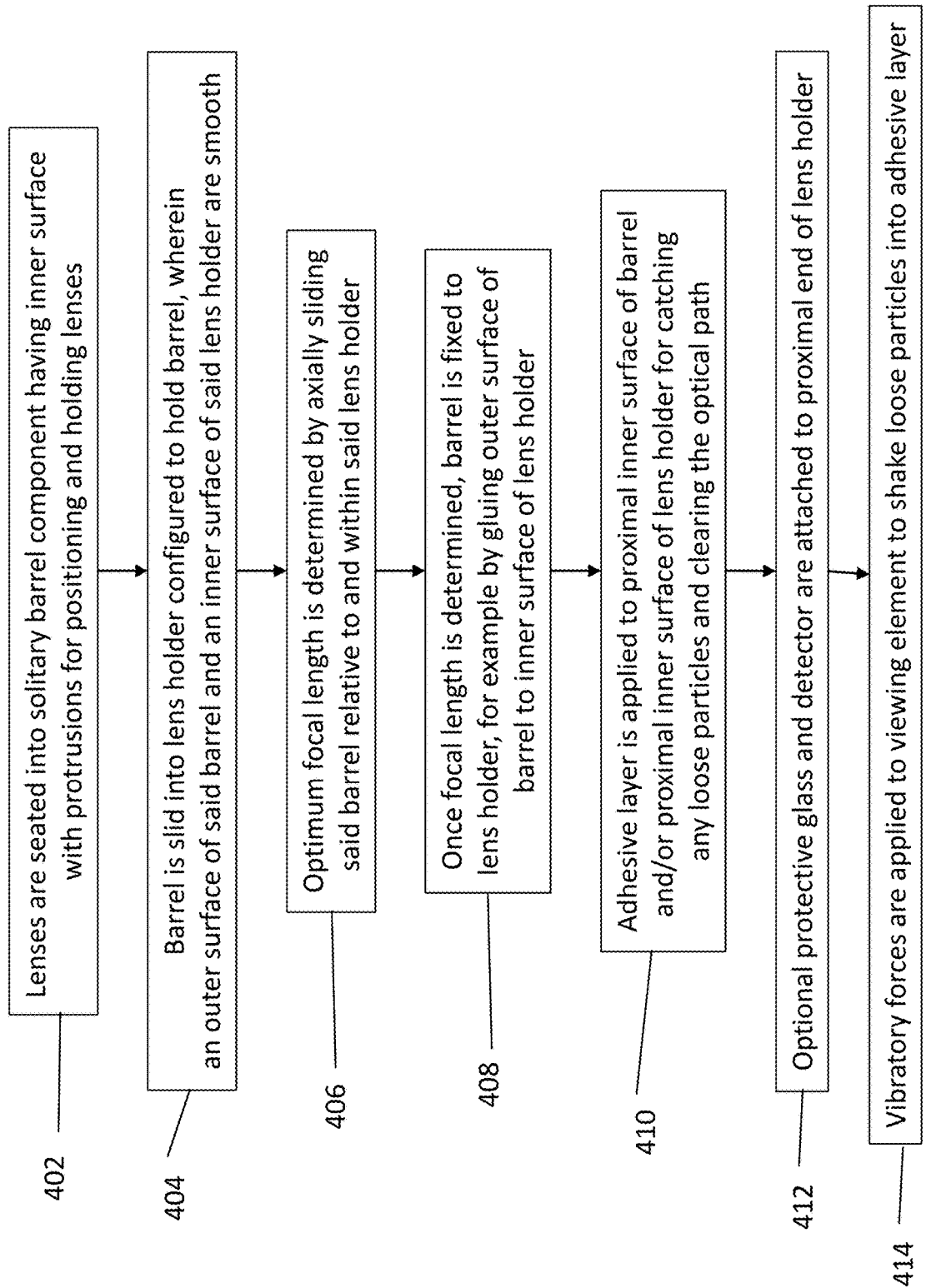

OPTICAL SYSTEM FOR AN ENDOSCOPE

CROSS-REFERENCE

The present application relies on U.S. Patent Provisional Application No. 62/120,141, entitled "Optical System for an Endoscope", and filed on Feb. 24, 2015, for priority.

In addition, the present application relates to U.S. patent application Ser. No. 13/882,004, entitled "Optical Systems for Multi-Sensor Endoscopes" and filed on May 23, 2013, which is a 371 National Stage Entry of PCT Application Number PCT/IL2011/000832, of the same title and filed on Oct. 27, 2011, which relies upon U.S. Provisional Patent Application No. 61/407,495, filed on Oct. 28, 2010, for priority.

The above-mentioned applications are incorporated herein by reference in their entirety.

FIELD

The present specification relates generally to endoscopy systems and more particularly, to an endoscopy system comprising a robust housing assembly for at least one viewing element wherein the housing assembly is consistent in shape and size, easy to clean and does not generate small unwanted particles from system wear and tear that may cause vision obstruction.

BACKGROUND

Endoscopes have attained great acceptance within the medical community since they provide a means to perform procedures with minimal patient trauma while enabling the physician to view the internal anatomy of the patient. Over the years, numerous endoscopes have been developed and categorized according to specific applications, such as cystoscopy, colonoscopy, laparoscopy, upper GI endoscopy and others. Endoscopes may be inserted into the body's natural orifices or through an incision in the skin.

An endoscope is usually an elongated tubular shaft, rigid or flexible, having a video camera or a fiber optic lens assembly at its distal end. The shaft is connected to a handle which sometimes includes an ocular for direct viewing. Viewing is also usually possible via an external screen. Various surgical tools may be inserted through a working channel in the endoscope to perform different surgical procedures.

In conventional endoscopes, the optical head, which is used to view the interior of a body cavity or lumen, such as a lower digestive track, is deployed in the front section of the endoscope that is inserted in the body. The optical head normally includes at least an illumination means to illuminate the object, an objective lens system, and a sensor array. The lens assembly in typical optical heads further comprises a lens housing and a barrel that supports the lenses. Current GI scopes use metal components for the housing and for other sections in the optical head that support the lenses. Commonly used metals are stainless steel and brass. They are machined into a required shape and fitted inside the scope. The metal components may be coated, blackened, polished, and treated in different ways. However, over time, small parts of these components wear out and the resulting particulate debris may interfere with, and get sensed by, the sensor. Burrs and other particles falling off from the lens housing components find their way onto the optical sensor. These particles show on the imaging monitors used by the physician. Additionally, machining metal components results in slight differences in shape and/or size with each machine, resulting in inconsistent components. The barrels used in lens assemblies often include two separate components comprising the barrel itself and an adapter within the barrel to hold the lenses. The outer surface of the barrel is typically threaded to match a threaded inner surface of the lens holder. The barrel is limited to spiral movement within the lens holder along these threaded surfaces. The threaded surfaces introduce further points for the creation burrs and particles as described above.

Therefore, there is a need in the art for endoscope components, and specifically lens assembly components, that are manufactured with consistency and, once embedded inside the scope, remain clean and/or are easy to clean. There is also a need for a lens assembly comprising a single barrel component having a formed inner surface for seating lenses, thereby eliminating the requirement of an adapter and reducing the overall number of lens assembly components. Such a lens assembly would also include a smooth barrel outer surface and a smooth lens holder inner surface to allow for greater freedom in movement of the barrel relative to the lens assembly and to reduce the likelihood of particles falling off either component and onto the optical sensor. There is also a need for endoscopes, such as colonoscopes, gastroscopes, bronchoscopes, and the like, that enable efficient packing of all necessary lens elements in the tip section while maintaining their functionality.

SUMMARY

The following embodiments and aspects thereof are described and illustrated in conjunction with systems, tools and methods, which are meant to be exemplary and illustrative, not limiting in scope. The present application discloses numerous embodiments.

In some embodiments, the present specification discloses a lens assembly manufactured by a process of: forming a barrel having a length, a proximal end, a distal end, an inner surface profile and an outer surface; placing a plurality of lenses into said barrel wherein said inner surface profile of said barrel is configured to receive and hold said lenses; sliding said barrel into a lens holder having an inner surface, a proximal end and a distal end; setting an optimum focal length by axially moving said barrel relative to and within said lens holder; and fixedly securing the barrel to the lens holder.

Optionally, the process further comprises applying an adhesive layer to an inner surface of the proximal end of the barrel or an inner surface of the proximal end of the lens holder after fixedly securing the barrel to the lens holder. Optionally, the adhesive layer has a thickness in a range of 20 µm to 50 µm. Optionally, the adhesive layer comprises of any one or combination of acryl, silicon, a pressure sensitive adhesive, and gel.

Optionally, the process includes applying vibratory forces to the lens assembly to shake loose particles into said adhesive layer. Optionally, said vibratory forces range from 20 kHz to 1 MHz.

Optionally, said process further comprises attaching a protective glass and a detector to the proximal end of said lens holder.

Optionally, the inner surface profile of said barrel comprises a plurality of protruded portions which provide support to position said plurality of lenses in the assembly. Optionally, said barrel has a thickness which varies along its length.

Optionally, said outer surface of said barrel and said inner surface of said lens holder are substantially smooth to allow for movement of said barrel relative to said lens holder and for setting said optimum focal length prior to fixedly securing said barrel to said lens holder.

Optionally, said process further comprises forming said inner surface profile of said barrel by milling, turning, injection molding, metal injection molding (MIM), or casting.

Optionally, said barrel comprises a non-reflective material to reduce reflections within said lens assembly.

Optionally, said process further comprises installing said lens assembly in an endoscope.

In some embodiments, the present specification discloses a viewing element for an endoscope made by a process comprising: forming a barrel having a length, a proximal end, a distal end, an inner surface profile and an outer surface; placing a plurality of lenses into said barrel wherein said inner surface profile of said barrel is configured to receive and hold said lenses; sliding said barrel into a lens holder having an inner surface, a proximal end and a distal end; setting an optimum focal length by axially moving said barrel relative to and within said lens holder; fixedly securing the barrel to the lens holder; applying an adhesive layer to an inner surface of the proximal end of the barrel and/or an inner surface of the proximal end of the lens holder; attaching a detector array to the proximal end of the lens holder; and, applying vibratory forces to the viewing element to shake loose internal particulate matter particles into the adhesive layer.

Optionally, the adhesive layer has a thickness in a range of 20 μm to 50 μm.

Optionally, the adhesive layer comprises any one or combination of acryl, silicon, a pressure sensitive adhesive, and gel.

Optionally, said vibratory forces range from 20 kHz to 1 MHz.

Optionally, said outer surface of said barrel and said inner surface of said lens holder are substantially smooth to allow for movement of said barrel relative to said lens holder and for setting said optimum focal length prior to fixedly securing said barrel to said lens holder.

Optionally, said inner surface profile of said barrel is formed by milling, turning, injection molding, metal injection molding (MIM), or casting.

Optionally, the inner surface profile of said barrel comprises a plurality of protruded portions which provide support to position said plurality of lenses in the viewing element.

The aforementioned and other embodiments of the present shall be described in greater depth in the drawings and detailed description provided below.

BRIEF DESCRIPTION OF THE DRAWINGS

These and other features and advantages of the present invention will be appreciated, as they become better understood by reference to the following detailed description when considered in connection with the accompanying drawing, wherein:

FIG. 4 is a flow chart listing the steps involved in a method of assembling a viewing element in accordance with one embodiment of the present specification.

DETAILED DESCRIPTION

Figure 1A:
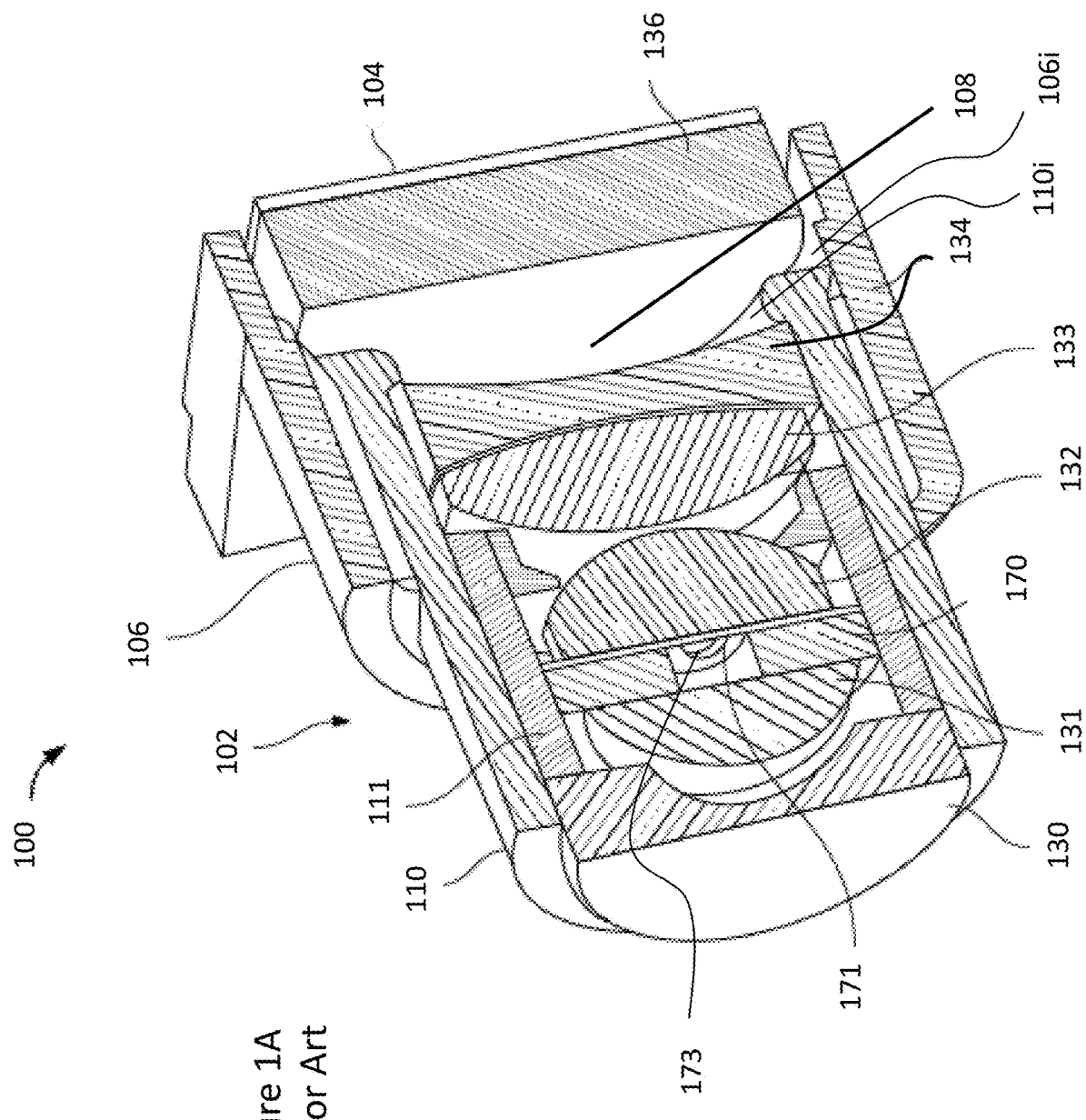
FIG. 1A schematically depicts a cross section of a lens assembly and detector array of a viewing element.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention. In the description and claims of the application, each of the words "comprise" "include" and "have", and forms thereof, are not necessarily limited to members in a list with which the words may be associated.

As used herein, the indefinite articles "a" and "an" mean "at least one" or "one or more" unless the context clearly dictates otherwise.

As used in this specification, the term "camera" is used to describe a device for capturing light. Thus, a camera, in some embodiments, comprises at least one optical lens assembly. In some embodiments, the term "camera' is used to describe an optical lens assembly and its associated image sensor. In some embodiments, the term "camera" is used to describe an optical imaging system, such as a lens assembly or assemblies and associated solid state detector arrays. In some embodiments, the terms "viewing element" and "camera" are used interchangeably.

As used in the specification, the term "optical assembly" is used to describe a set of components that allows the endoscopic device to capture light and transform that light into at least one image. In some embodiments, lenses/optical elements are employed to capture light and image capturing devices, such as sensors, are employed to transform that light into at least one image.

Image capturing devices may be Charged Coupled Devices (CCDs) or Complementary Metal Oxide Semiconductor (CMOS) image sensors, or other suitable devices having a light sensitive surface usable for capturing an image. In some embodiments, a sensor, such as a Charge Coupled Device (CCD) or a Complementary Metal Oxide Semiconductor (CMOS) image sensor (for detecting the reflected light received by an optical element), is employed.

In some embodiments, an optical element comprises a plurality of optics, such as lens assemblies, lenses and protective glass, and is configured to receive reflected light from at least one target object.

In some embodiments, an optical assembly, as used in the specification, comprises at least one lens assembly, its associated sensor(s), and its associated circuit board. In some embodiments, an "optical assembly" comprises more than one viewing element or camera, associated sensor(s), and associated circuit board(s). In some embodiments, an "optical assembly" comprises a front viewing element, its associated sensor, and its associated circuit board. In some embodiments, an "optical assembly" comprises a front viewing element, its associated sensors, and its associated circuit board and/or at least one side viewing element, its associated sensors and its associated circuit boards. Further, in some embodiments, the optical assembly is associated with at least one illuminator for illuminating the field of view. Thus, for example, in an embodiment, a front-pointing optical assembly includes a front-pointing viewing element with associated sensor and associated circuit board and is associated with at least one illuminator.

It is noted that the term "endoscope" as mentioned to herein may refer particularly to a colonoscope, according to some embodiments, but is not limited only to colonoscopes. The term "endoscope" may refer to any instrument used to examine the interior of a hollow organ or cavity of the body.

Endoscopes that are currently being used may have a front viewing element and side viewing elements for viewing the internal organs, illuminators, a fluid injector to clean the lens of the viewing elements, and a working channel for insertion of surgical tools. The illuminators commonly used are fiber optics that transmit light, generated remotely, to the endoscope tip section. The use of light-emitting diodes (LEDs) for illumination is also known.

A tip section of the endoscope assembly may be inserted into a patient's body through a natural body orifice, such as the mouth, nose, urethra, vagina, or anus.

In accordance with an embodiment of the present specification, a tip cover houses the tip section. In an embodiment, the tip section, with the tip cover, is turned or maneuvered by way of a flexible shaft, which may also be referred to as a bending section, which may be, for example, a vertebra mechanism. In an embodiment, the tip cover is configured to fit over the inner parts of the tip section, including an electronic circuit board assembly and a fluid channeling component, and to provide protection to the internal components of the tip section when it is inside a body cavity. The endoscope can then perform diagnostic or surgical procedures inside the body cavity. The tip section carries one or more viewing elements, such as cameras and sensors, to view areas inside body cavities that are the target of these procedures. Viewing elements may include an image sensor, such as but not limited to a Charge Coupled Device (CCD) or a Complementary Metal Oxide Semiconductor (CMOS) image sensor.

In an embodiment, the tip cover includes panels having a transparent surface, window or opening for optical lens assemblies and for the illuminators of viewing elements. In an embodiment, the panels and viewing elements are located at the front and sides of the tip section. In some embodiments, the optical lens assemblies include a plurality of lenses, static or movable, providing different fields of view.

In an embodiment, an electronic circuit board assembly is configured to carry the viewing elements, which view through openings on the panels. In an embodiment, the electronic circuit board assembly is configured to carry illuminators that are able to provide illumination through illuminator optical windows. The illuminators are associated with viewing elements, and are positioned to illuminate the viewing elements' fields of view.

In some embodiments, one or more illuminators illuminate the viewing fields of the viewing elements. In an embodiment, the illuminators are fiber optic illuminators that carry light from remote sources. The optical fibers are light carriers that carry light from a remotely located light source to the illuminators. The optical fibers extend along an insertion tube between the tip section at a distal end of the endoscope, and a handle at a proximal end. The optical fibers further travel through the umbilical tube into a main control body where the source of light may be located. In an alternative embodiment, the light source of the optical fibers is located in the handle. An umbilical/utility tube connects the handle to a main control unit. The main control unit enables control of several functions of the endoscope assembly, including power delivered and communication of signals between the endoscope and its display, among others. In an embodiment, the illuminators comprise LEDs emitting in white light, IR, UV, or other energies.

Figure 1B:
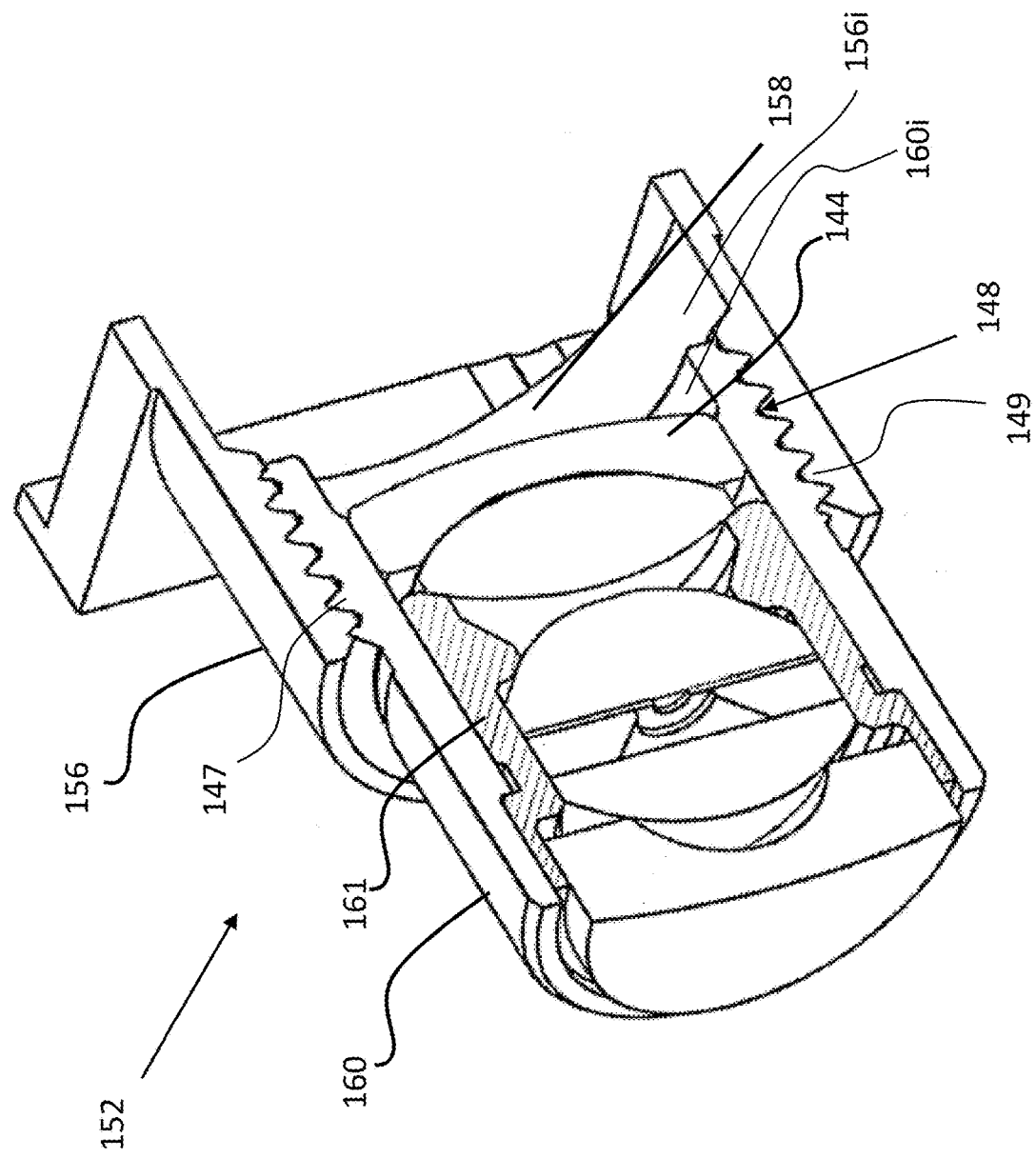
FIG. 1B schematically depicts a cross section of another lens assembly of a viewing element.
Figure 1C:
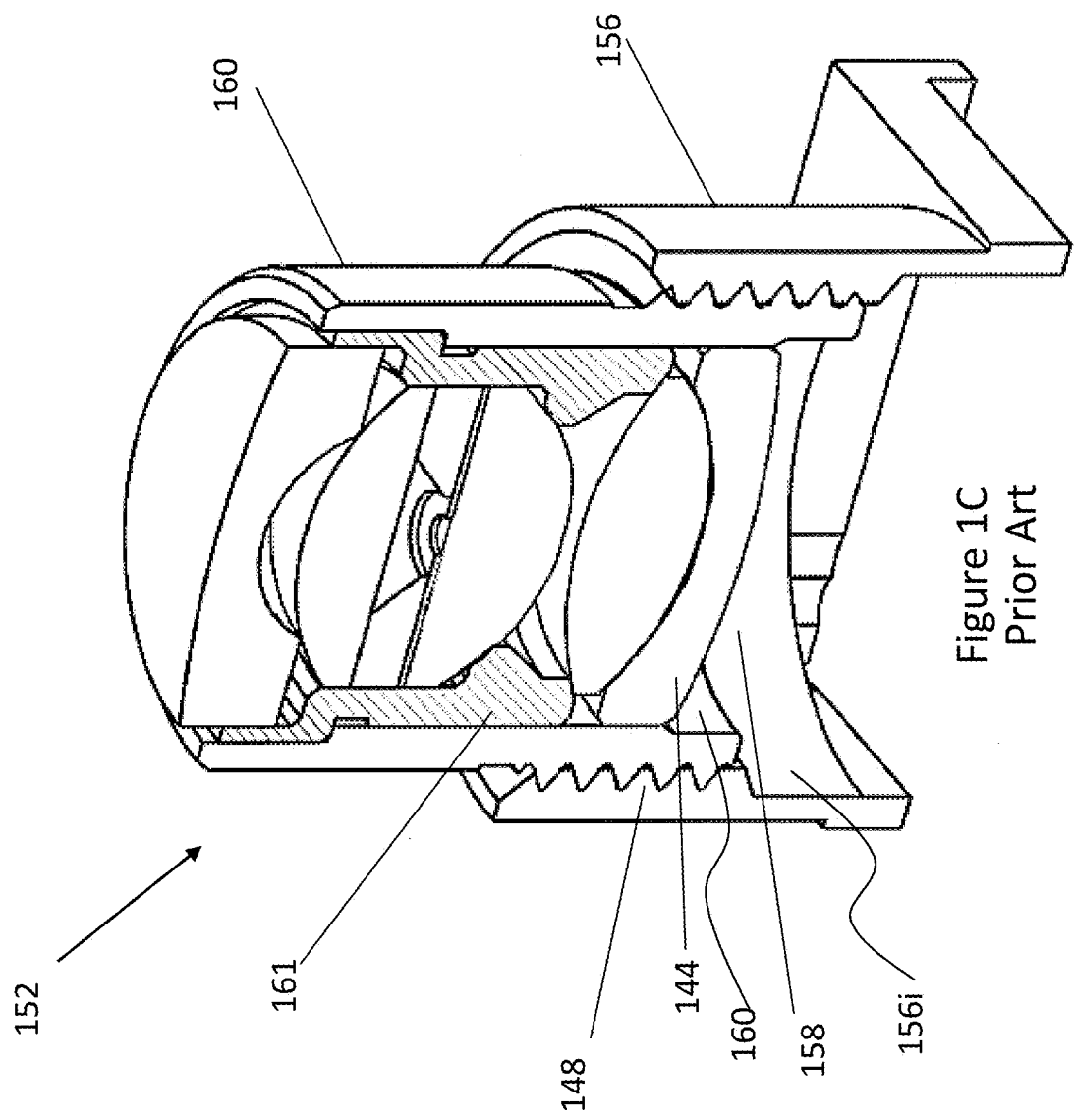
FIG. 1C depicts a rotated view of the cross section of the lens assembly of FIG. 1B.
Figure 1D:
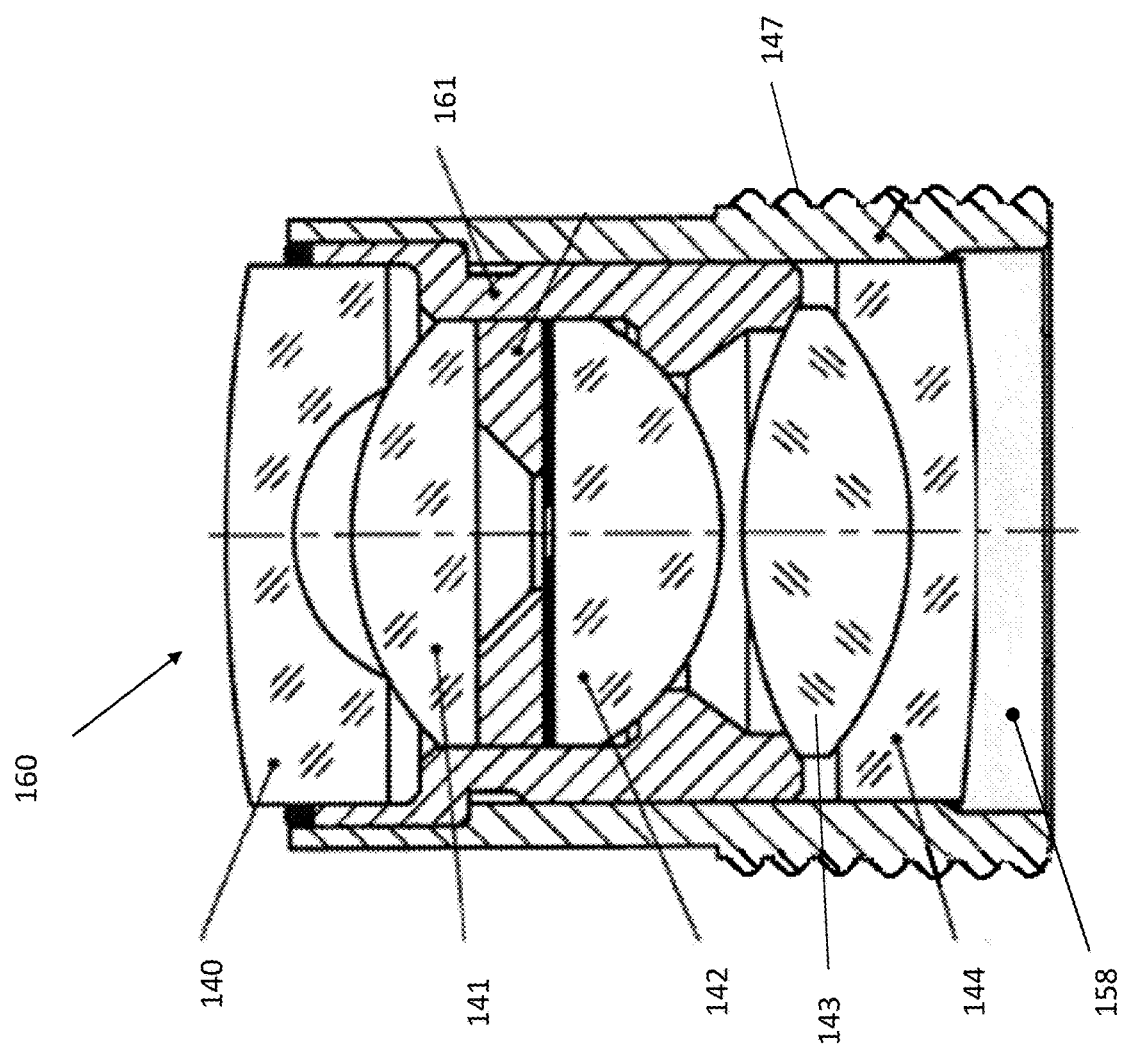
FIG. 1D depicts a view of the cross section of the barrel of the lens assembly of FIGS. 1B and 1C.

FIGS. 1A and 1B schematically depict a cross section of a lens assembly 102 and detector array 104 of viewing element 100, and a lens assembly 152, respectively. FIG. 1C depicts a rotated cross-sectional view of lens assembly 152 of FIG. 1B. FIG. 1D depicts a cross-sectional view of the barrel of lens assembly 152 of FIGS. 1B and 1C.

Referring to FIG. 1A, viewing element 100 may be one of a forward-looking viewing element or a side looking viewing element. Viewing element 100 is provided with an optical imaging system such as a lens assembly (system) 102 and a solid-state detector array 104. Lens assembly 102 comprises a set of lenses 130, 131, 132, 133, and 134 and a protective glass 136. Lenses 130, 131, 132, 133, and 134 may have similar configurations or may be different.

It should be noted that viewing element 100 might be of any focal length, resolution, light sensitivity, pixel size and pixel number, focal distance, and depth of field, which is suitable for the desired purpose. Differences in focusing distances are achieved, for example, by (slightly) changing the distance between the lenses that comprise the lens assembly 102, or between lens assembly 102 and detector array 104.

Light is provided by light emitting diodes (LEDs) that illuminate the fields of view. According to some applications, white light LEDs are used. According to other applications, other colors of LEDs or any combination of LEDs are used (for example, red, green, blue, infrared, and ultraviolet).

A stop component 171 between lenses 131 and 132 acts as a stop and affects the focal range of the viewing element 100. It should be appreciated that the term focal length may be used to refer to the distance from a lens to a sensor or may be used to refer to the distance, from the lens, over which an object remains in focus. One of ordinary skill in the art would understand what definition for focal length is being used based on the context and distances discussed.

The stop component 171 includes an opening or hole 173 and the size of said opening or hole 173, along with the relative distance of the stop component 171 from lenses 131 and 132, determine the effect on focal range (the distance between the closest object and farther objects that can be imaged without excessive blurring caused by being out of optimal focusing of the lens system). Spacer 170 is positioned between lenses 131 and 132 and assists with positioning of the stop component 171. As seen in FIG. 1A, the stop component 171 is positioned in a central opening of spacer 170.

Lenses 130, 131, 132, 133, and 134 are situated within a barrel 110 and connected thereto (for example, glued or otherwise adhered in barrel 110). In the viewing element described in FIG. 1A, lens assembly 102 includes an adapter 111, positioned within barrel 110. Adapter 111 is configured to adjust the location of one or more of lenses 130, 131, 132, 133 and 134 and adjust the distance between them. In another version of the viewing element described in FIG. 1A, adapter 111 is configured to function as a distance spacer (in this case, between lenses 132 and 133). The adapter 111 is used to set the positions of one or more of lenses 130, 131, 132, 133 and 134 and the distances between them during manufacture of the lens assembly 102. Once the lens assembly 102 is fully assembled, these positions and distances cannot be changed, relative to each other. Further, the adapter 111 typically comprises a black metallic element that serves as a non-reflective element surrounding the optical path. Typically, the barrel 110 is manufactured from a non-dark stainless steel material that reflects light. The inclusion of a black colored adapter 111 serves to minimize reflected light in the lens assembly 102, while also positioning the lenses 130, 131, 132, 133 and 134. Protective glass 136 is positioned in proximity to solid-state detector array 104 and is optionally attached thereto. Protective glass 136 provides protection to detector array 104 against any particles, debris, or any other component that may be loosely situated within lens assembly 102.

The focal distance (the distance to the object to be optimally focused by the lens system) is changed by changing the distance between lens 134 and protective glass 136. As lens 134 is fixed to barrel 110, and protective glass 136 is statically fixed to a lens holder 106, this distance is varied by changing the relative positioning of the barrel 110 with respect to lens holder 106. The lens array, including lenses 130 to 134, is fixed within barrel 110. As a result, the distance between the lens array and protective glass 136 is varied only by allowing movement between barrel 110 and holder 106. A space 108 between lens 134 and protective glass 136 may be an empty space or may be filled with glass or other transparent material, or a tubular spacer may be inserted. Optionally, optical filters are placed within the space. The space 108 exists as a result of the optical design and the positioning of the focal point far from lens 134. Protective glass 136 provides no optical benefit but functions to protect the components of the viewing element and, in FIG. 1A, is depicted with the minimum thickness required.

FIG. 1B shows a lens assembly 152 of a viewing element with a threaded junction 148 between the barrel 160 and the lens holder 156 and FIG. 1C is a rotated view of the lens assembly 152 of FIG. 1B. The barrel 160 has a threaded external surface 147. For example, the barrel 160 has an external acme thread as a part of its external periphery. Similarly, lens holder 156 has a matching threaded internal surface 149. For example, the lens holder 156 has a matching internal acme thread as a part of its internal periphery. The barrel 160 is rotated in either a clockwise or counterclockwise direction to enable movement along threaded junction 148 between barrel 160 and lens holder 156. Thus, threaded junction 148 enables changing the relative positioning of barrel 160 with respect to lens holder 156. As a result, the focal distance can be changed by changing the distance between lens 144 and a protective glass and detector array (shown in FIG. 1A). Barrel 160 and lens holder 156 are customarily made of metal, predominantly stainless steel and brass. They are often machined into shape. Further, they may be coated, blackened, polished and treated in other ways. However, the treatment may leave small particles between or along threaded junction 148 which are not detected during the assembly of lens assembly 152. Such small particles affect the quality of lens assembly 152 by creating falling debris which may land on the protective glass or detector array of a fully assembled viewing element and obscure the view. An adapter 161, comprising a separate component distinct from the barrel 160, is positioned within the barrel 160 and configured to hold the lenses, including lens 144, in place. Similar to lens assembly 102 of FIG. 1A, the adapter 161 of the lens assembly 152 of FIG. 1B usually includes a black colored inner surface to reduce reflected light in the optical path. A space 158 is located proximal to lens 144.

FIG. 1D depicts a cross-sectional view of the barrel 160 of the lens assembly of FIGS. 1B and 1C. A separate, distinct adapter 161 is positioned inside the barrel 160 and is used to position at least one of lenses 140, 141, 142, 143 and 144 within said barrel 160. A space 158 is located proximal to lens 144. The barrel 160 includes a threaded outer surface 147 for joining with a matching threaded surface of a lens holder as described with reference to FIGS. 1B and 1C.

Figure 2A:
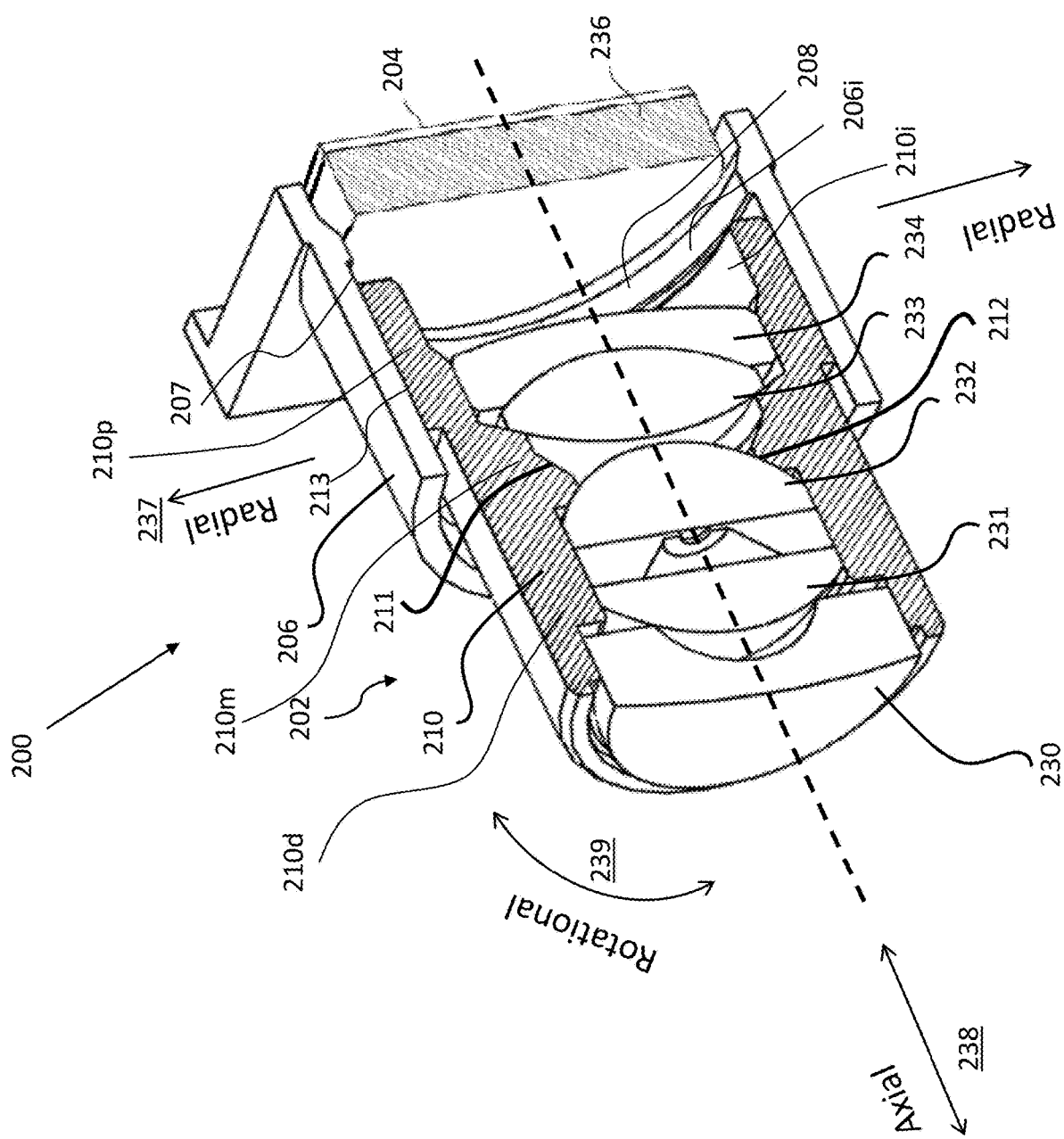
FIG. 2A schematically depicts a cross section of a lens assembly and detector array of a viewing element, according to one embodiment of the current specification.
Figure 2B:
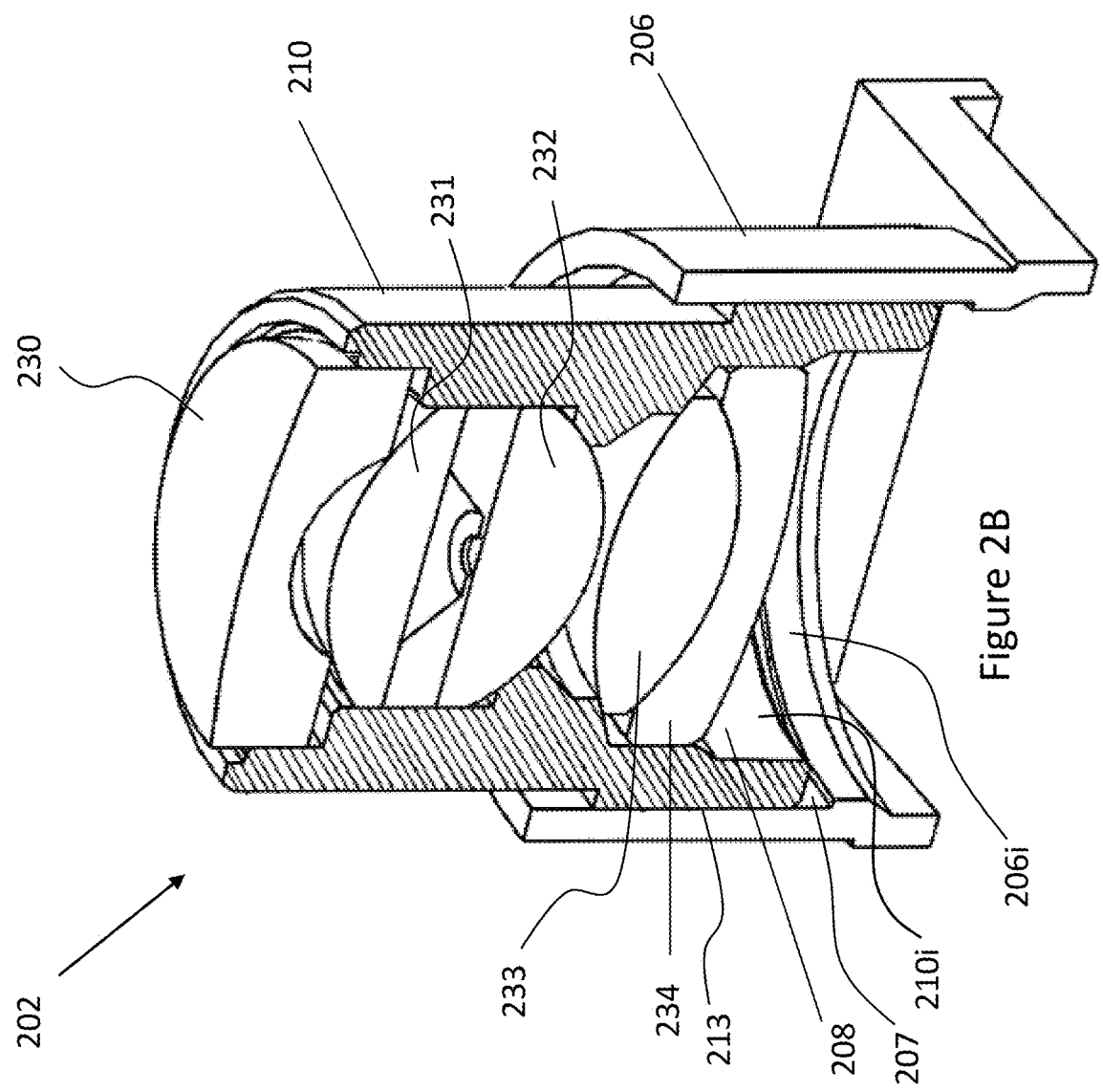
FIG. 2B depicts a rotated view of the cross section of the lens assembly of FIG. 2A.

FIG. 2A schematically depicts a cross section of a lens assembly 202 and detector array 204 of a viewing element 200, according to one embodiment of the current specification, and FIG. 2B is a rotated view of the lens assembly 202 of FIG. 2A. Referring to FIG. 2A, viewing element 200 may be one of a forward-looking viewing element or a side looking viewing element, in accordance with various embodiments. Referring to FIGS. 2A and 2B, lens assembly 202 comprises a set of lenses 230, 231, 232, 233, and 234, similar to lenses 130, 131, 132, 133, and 134 of FIG. 1A and lenses 140, 141, 142, 143, and 144 of FIG. 1D. In some embodiments, lenses 230, 231, 232, 233, and 234 are placed adjacent to each other such that lens 230 is placed near the distal tip of the lens assembly 202 and is first to receive light from of a target object or scene that is being imaged. Therefore, lens 234 becomes the last lens to receive the same light, after the light sequentially passes through lenses 230, 231, 232, and 233, which are placed on one side of lens 234. Subsequently, light passes through lens 234 to reach a detector array.

It should be noted that according to some embodiments of the specification, referring to FIG. 2A, viewing element 200 might be of any focal length, resolution, light sensitivity, pixel size and pixel number, focal distance and depth of field, which is suitable for the purpose of this specification.

In embodiments throughout this specification, the term focal length may be used to refer to the distance from a lens to a sensor or may be used to refer to the distance, from the lens, over which an object remains in focus. One of ordinary skill in the art would understand what definition for focal length is being used based on the context and distances discussed.

In some embodiments, the differences in focusing distances are achieved by moving the barrel 210 within and relative to lens holder 206 thereby moving lenses 230, 231, 232, 233, and 234 relative to detector array 204 and protective glass 236. In some embodiments, detector array 204 and protective glass 236 are attached to the lens holder 206.

Referring again to FIGS. 2A and 2B, in some embodiments, lenses 230, 231, 232, 233, and 234 are situated within barrel 210 and connected thereto (for example, glued in barrel 210). In various embodiments, the lenses 230, 231, 232, 233, and 234 are coupled by means of glue, or any other material that enables fixing to barrel 210 without affecting the optical characteristics of lens assembly 202. Lenses 230, 231, 232, 233, and 234 are connected to an inner surface 211 of barrel 210.

In some embodiments, lens holder 206 encompasses barrel 210 such that at least a portion of an outer surface 213 of barrel 210 is in contact with and encased by an inner surface (or periphery) 207 of lens holder 206. In embodiments, the inner surface 207 of lens holder 206 is formed to the same shape of the outer surface 213 of barrel 210 to enable its encasement. In some embodiments, lens holder 206 is cylindrically shaped to cover a portion of barrel 210 which has an outer surface 213 also shaped like a cylinder. In some embodiments, barrel 210 is free to move in axial 238 as well as rotational 239 directions independently or at the same time. In addition, radial movement 237 of barrel 210 is limited by holder 206. Having a single barrel 210 with molded inner surface 211 serves to increase the accuracy of the lenses' positions relative to each other by seating the lenses more accurately compared to prior art barrels with adapters. In an embodiment of the present specification, the inner surface 211 of barrel 210 is shaped according to the position and size of the plurality of lenses 230, 231, 232, 233, and 234 such that its inner surface 211 is in contact with outer edges of lenses 230, 231, 232, 233, and 234.

Barrel 210 is different from barrels 110 and 160 of the conventional configurations in that the two separate components of the conventional barrels, namely barrels 110, 160 and adapters 111, 161 of FIGS. 1A and 1B-1D respectively, are one unified component in barrel 210. In other words, in an embodiment, the barrel 210 of the lens assembly 202 of the present specification is a single, unitary structure. Conventional barrels of current endoscope viewing elements comprise two components, the barrel itself and an adapter within, as discussed with reference to FIGS. 1A-1D.

Referring to FIG. 2A, in an embodiment, the barrel 210 is configured to adjust the location of one or more of lenses 230, 231, 232, 233, and 234 and also adjust the distance between a lens, such as lens 234, and a protective glass 236 and detector array 204, via a shaped internal periphery, or inner formed surface 211. The inner formed surface 211 achieves an improved function of the adapter encountered in the prior art, particularly, with respect to positioning and fixing the lenses within the barrel 210. In various embodiments, the inner formed surface 211 of barrel 210 holds the lenses 230, 231, 232, 233, and 234 and defines their positions in at least two ways. Firstly, the inner formed surface 211 defines lenses 230, 231, 232, 233, and 234 radial positions, wherein the inner diameter of barrel 210 confines each lens to be concentric with it. Secondly, the inner formed surface 211 defines lenses 230, 231, 232, 233, and 234 axial positions. For example, in an embodiment, lenses 232 and 233 are axially defined in position by inclined surfaces that support them at a defined axial position. The remaining lenses 230, 231 and 234 may be defined axially by stacking on top of lens 232 or 233 respectively. In some embodiments, the barrel 210 has a varying thickness throughout its length such that the inner formed surface 211 extends further into the optical path at specific points along said length (also described further below as projections 212). For example, in an embodiment, a first proximal region 210$p$ has a first thickness which is less than a second thickness of a second middle region 210$m$. A third distal region 210$d$ has a third thickness which is greater than said first thickness but less than said second thickness. In some embodiments, the inner surface 211 of the barrel 210 extends proximally beyond lens 234 and into space 208. This is to allow for placement of all the lenses 230, 231, 232, 233, and 234 within the solitary barrel 210. As seen in FIGS. 1A-1D, the adapter 111, 161 ends in the proximal direction before corresponding lens 134, 144. Therefore, referring to FIGS. 1A-1D and 2A simultaneously, only some of the lenses are positioned within the adapter 111, 161 in the prior art while all of the lenses are positioned within the inner surface 211 of the barrel 210 of the lens assemblies of some embodiments of the present specification.

In various embodiments, the barrel 210 is composed of material having a black color such that light reflection within the optical path is reduced by the non-reflective inner surface 211 of the barrel 210. In embodiments, lens array including lenses 230 to 234 are fixed to barrel 210 and their position relative to each other is also fixed. The position of the lenses is defined by the design of the viewing element and the inner surface 211 of the barrel 210 allows for accurate and consistent placement of the lenses as per the specific design. In an embodiment, the position of each lens 230, 231, 232, 233, and 234 and the distance between each lens 230, 231, 232, 233, and 234 in the lens array are adjusted during manufacturing and assembly of the various optical components by modifying the profile of the inner surface 211.

In an embodiment, at the time of manufacturing, the geometry of barrel 210 is configured to include one or more projections 212 from the internal periphery, or internal surface 211 of the barrel 210. In various embodiments, these projections 212 are formed by any one or combination of milling, turning, injection molding, metal injection molding (MIM), and casting. The projection(s) 212 functions as a distance spacer (referring to FIG. 2A, between lenses 232 and 233). The geometry of the barrel 210 defines the distance between lenses 232 and 233 and the internal periphery, or internal surface 211, includes projections 212 designated as seats for the various lenses. The inner surface 211 and projections 212 of the barrel 210 allow for fixed positioning and spacing of the lenses, similar to the adapter of the prior art, while simultaneously eliminating the need for said adapter by providing a single barrel component. In addition, the fixed positioning and spacing of the lenses is more accurate with the single barrel component compared to the prior are barrel with adapter. The single barrel configuration reduces the overall parts number and enables easier manufacturing.

In an embodiment, a protective glass 236 is positioned in proximity to a solid-state detector array 204 and is optionally attached thereto. In embodiments, the protective glass 236 is placed at a distance from lens 234 and allows the light from the lenses to pass through it towards the detector array 204. In embodiments, the distance between detector array 204 and therefore also protective glass 236, from lens 234 is fixed after determining an optimal focus for viewing element 200. The barrel 210 may be fixed to the lens holder 206 to keep this determined optimal focus distant constant and, in embodiments, is fixed by gluing or other securing methods as discussed further below. In embodiments of the present specification, the protective glass 236 provides protection to detector array 204 against any particles, debris, or any other component that may be loosely situated within lens assembly 202 and cause degradation in the quality of viewing element 200.

The protective glass 236 is situated between and in proximity to lens 234 and solid-state detector array 204 and is optionally attached thereto. In an embodiment, a space 208 between lens 234 and protective glass 236 is empty. In another embodiment, the space 208 is filled with glass or other transparent material, or a tubular spacer is inserted in the space 208.

In some embodiments, an adhesive layer is applied within space 208, along an inner layer of the barrel 210 and/or lens holder 206. In some embodiments, the space 208 extends within both the proximal end of the barrel 210 and the proximal end of the lens holder 206 and the adhesive layer is applied to an inner layer 210i of the barrel 210 and an inner layer 206i of the lens holder 206. In other embodiments, the space is located only within the proximal end of the barrel and the adhesive layer is applied only to an inner layer of the barrel. In still other embodiments, the space is located only within the proximal end of the lens holder and the adhesive layer is applied only to an inner layer of the lens holder. In all of the embodiments with an adhesive layer, the adhesive layer is not placed on lens 234 or protective glass 236.

The adhesive layer is composed of a material that does not omit particle collection (does not cause contamination) and that is strong enough to hold particles (grab and hold contaminates in the optical path). In various embodiments, the adhesive layer is composed of any one or combination of acryl, silicon, a pressure sensitive adhesive, and gel. In an embodiment, the adhesive layer comprises adhesives that possess viscoelasticity characteristics. In some embodiments, adhesives are tape type, and do not dry at room temperature. In various embodiments, the adhesive layer has a thickness which is thick enough to effectively and efficiently grab and hold any loose particles or debris while also being thin enough that the adhesive layer does not enter into the field of view of the viewing element. In various embodiments, the adhesive layer has a thickness in a range of 20 μm to 50 μm.

In embodiments, an adhesive layer on the lower and inner periphery 206i of lens holder 206 and/or lower and inner periphery 210i of barrel 210, such as within space 208, provides a means to remove obstructive components from the optical path of vision. Small particles, debris, or burr that may be generated from the optical components may create obstacles within the optical path of viewing element 200. In embodiments, a vibratory movement or any other movement, such as that resembling a 'shake', results in movement of obstructive components towards the adhesive layer within space 208. Once the obstructive components adhere to the adhesive layer, the optical path of vision remains clear and free of obstacles. In an embodiment, obstacles are removed by placing viewing element 200 on a centrifuge motor. In this embodiment, the centrifuge forces shifts the obstacles from the space 208 between lenses and the detector array, towards the periphery of space 208. At the periphery, the adhesive layer enables adhesion of the obstacles to the periphery, thus clearing the view. In various embodiments, the viewing element is subjected to vibratory forces to shake any loose particles toward the adhesive layer where they become stuck to provide a clear optical path. In some embodiments, vibratory forces ranging from 20 kHz to 1 MHz are applied to the viewing element. In other embodiments, the viewing element is subjected for 10 minutes to vibratory forces having a root-mean-square acceleration ($G_{rms}$) vibration level of 10, 15, 20, 25, or 30 to shake loose particles to the adhesive layer with no structural or mechanical damage.

FIG. 2B illustrates a rotated view of lens assembly 202 of the viewing element of FIG. 2A. Space 208, between lens 234 and the protective glass (not shown) is seen clearly. An adhesive layer is positioned on an inner surface 210i of the barrel 210 and/or an inner surface 206i of the lens holder 206.

Figure 3:
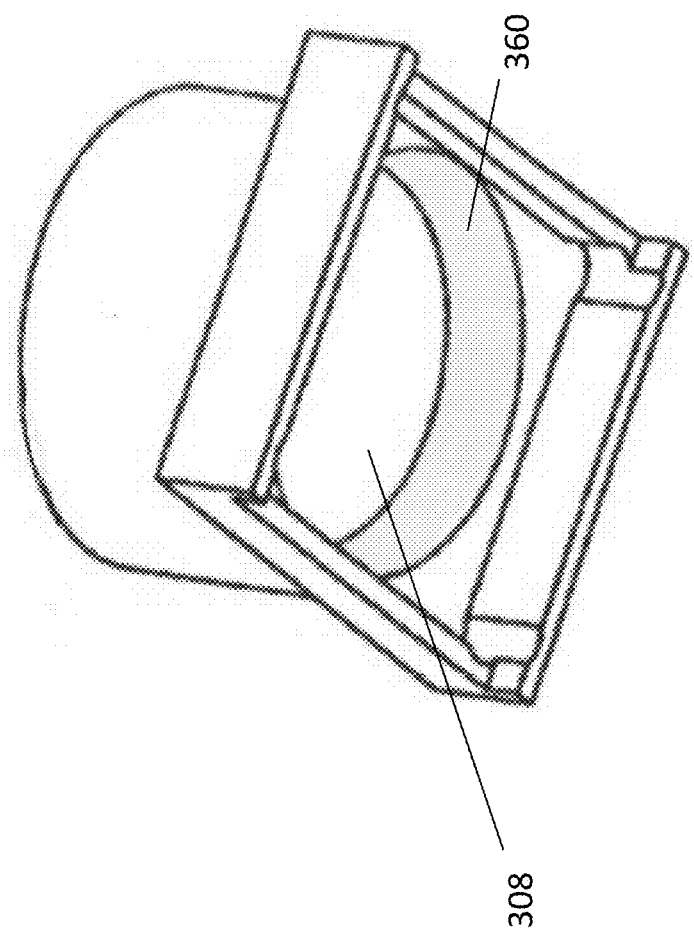
FIG. 3 illustrates an adhesive layer applied at a space between the lenses and sensor of viewing elements in accordance with embodiments described in the context of FIGS. 2A and 2B.

In some embodiments, such as those described in FIGS. 1A, 1B, 1C, and 1D, including space 108, 158 similar to space 208, also utilize an adhesive layer as described herein. For example, referring to FIGS. 1A, 1B and 1C simultaneously, an adhesive layer can be applied to inner surface 110i, 160i of barrel 110, 160 and/or inner surface 106i, 156i of lens holder 106, 156 for removing debris and other obstacles that may be loosely situated within lens assembly 102, 152. The adhesive layer is not applied to lens 134, 144 or protective glass 136 (shown in FIG. 1A). FIG. 3 illustrates an adhesive layer 360 within a space 308 between lenses and sensor of viewing elements in accordance with embodiments described in context of FIGS. 1A, 1B, 1C, 1D, 2A, and 2B.

Referring back to FIG. 2A, in an embodiment, the focal distance is changed by changing the distance between lens 234 and protective glass 236. As lens 234 is fixed to barrel 210, and protective glass 236 is fixed to a lens holder 206, this distance can be varied by changing the relative positioning of the barrel 210 with respect to the protective glass 236.

In embodiments, lens assembly 202 has further components that are easily cleaned of small particles. For example, in an embodiment, an ultrasonic cleaning process is utilized to clean small particles. In some embodiments of the present specification, barrel 210 and lens holder 206 are manufactured using injection molding. In some embodiments, plastic is used for their injection molding. In various embodiments, plastic may include but is not limited to polysulfone (PSU), liquid crystalline polymer (LCP), or polyether ether ketone (PEEK). In an embodiment, the material used for the injection molding has characteristics that enable its application to be optimally suited to the compact environment within a viewing element of an endoscope. For example, the material retains its geometrical stability under temperature and humidity variations, has low water absorbance, is rigid, is opaque, is suitable for adhesive bindings, is suitable for manufacturing in miniature sizes, and has thin wall thickness.

As a result of injection molding, threads between barrel 210 and lens holder 206 are absent. In embodiments, these two components are connected to each other by glue, or any other method used to connect plastic components. Once glued together, the components are fixed relative to one another. For example, once an optimum focal distance has been determined, the barrel 210 and lens holder 206 can be glued together to keep the desired focal distance. The absence of a thread between the two components (barrel 210 and lens holder 206) reduces the amount of particles that might fall on the sensor surface, thus keeping the components clean and/or enabling easy cleaning. Additionally, in the prior art, the barrel can only be moved relative to the lens holder by rotating the barrel clockwise or counterclockwise to position the barrel further into or out of the holder, respectively. In the embodiments depicted in FIGS. 2A and 2B, the barrel is capable of moving in axial and rotational directions independently with respect to the lens holder. This allows for greater fine tuning of the positioning of the lens assembly during manufacturing.

FIG. 4 is a flow chart listing the steps involved in a method of assembling a viewing element in accordance with one embodiment of the present specification. At step 402, lenses are seated into a solitary barrel component having an inner surface with protrusions for positioning and holding the lenses. At step 404, the barrel is slid into a lens holder configured to hold the barrel, wherein an outer surface of the barrel and an inner surface of the lens holder are smooth. An optimum focal length is determined at step 406 by axially sliding said barrel relative to and within the lens holder. Once the focal length is determined, the barrel is fixed to the lens holder at step 408, for example by gluing the outer surface of the barrel to the inner surface of the lens holder. At step 410, an adhesive layer is applied to a proximal inner surface of the barrel and/or a proximal inner surface of the lens holder for catching any loose particles and clearing the optical path. An optional protective glass and detector are attached to the proximal end of the lens holder at step 412. Optionally, at step 414, vibratory forces are applied to the viewing element to shake any loose particles into the adhesive layer.

Plastic injected components have several advantages over their metal counterparts. Plastic injected components can have surfaces with a high surface roughness quality. In embodiments, higher surface roughness quality results in cleaner surfaces leading to fewer or no contaminants in assembled components. Additionally, injection molded components have consistently accurate dimensions. As a result, the possibility of misalignment occurring between components is reduced. The method of manufacturing plastic injection-molded components are advanced and allows relatively more control over the size of the components, as compared to conventional methods. Problems related to burs and other particles that fall off from the metal-based lens housing components, and onto the optical sensor, are addressed by the use of plastic injected components in accordance with embodiments of the present specification.

In some applications, the protective glass is a flat-flat optical element, acting primarily as a protection for the detector array, and may optionally be supplied with the array.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A lens assembly manufactured by a process of:
   forming a barrel having a length, a proximal end, a distal end, a radially inward facing surface, and a radially-outward facing surface;
   placing a plurality of lenses into said barrel wherein a profile of said radially inward facing surface of said barrel is configured to receive and hold said lenses;
   sliding said barrel into a holder having a radially inward facing surface, a proximal end, and a distal end;
   setting a focal length by axially moving said barrel relative to and within said holder;
   fixedly securing the barrel to the holder; and
   applying an adhesive layer to a proximal end of the radially inward facing surface of the barrel and/or a proximal end of the radially inward facing surface of the holder, wherein a radially inward facing surface of the adhesive layer remains exposed after fixedly securing the barrel to the holder.

2. The lens assembly of claim 1, wherein said adhesive layer has a thickness in a range of 20 μm to 50 μm.

3. The lens assembly of claim 1, wherein said adhesive layer comprises any one or combination of acryl, silicon, a pressure sensitive adhesive, and gel.

4. The lens assembly of claim 1, further comprising applying vibratory forces to the lens assembly to shake loose particles into said adhesive layer, and wherein the radially inward facing surface of the adhesive layer that remains exposed is configured to grab and hold the particles.

5. The lens assembly of claim 1 further comprising attaching a protective glass and a detector to the proximal end of said holder.

6. The lens assembly of claim 1, wherein the radially inward facing surface of said barrel comprises a plurality of protruded portions which provide support to position said plurality of lenses in the barrel.

7. The lens assembly of claim 1, wherein said barrel has a wall thickness, measured in a direction perpendicular to a central longitudinal axis of said barrel, which varies along a length of said barrel.

8. The lens assembly of claim 1, wherein said radially outward facing surface of said barrel and said radially inward facing surface of said holder are substantially smooth to allow for movement of said barrel relative to said holder, and for setting said focal length prior to fixedly securing said barrel to said holder.

9. The lens assembly of claim 1 further comprising forming said radially inward facing surface of said barrel by milling, turning, injection molding, metal injection molding (MIM), or casting.

10. The lens assembly of claim 1, wherein said barrel comprises a non-reflective material to reduce reflections within said lens assembly.

11. A viewing element for an endoscope made by a process comprising:
    forming a unitary and monolithic barrel having a length, a proximal end, a distal end, a radially inward facing surface surrounding a passageway, and a radially outward facing surface, wherein the passageway includes a central portion between the distal and proximal ends of the passageway, wherein the central portion includes a proximal portion with a first diameter, an intermediate portion with a second diameter, and a distal portion with a third diameter, and wherein the first, second, and third diameters are different;
    placing a plurality of lenses into said passageway of said barrel, wherein said radially inward facing surface of said barrel is configured to hold said lenses;
    sliding said barrel into a holder having a radially inward facing surface, a proximal end, and a distal end;
    setting a focal length by axially moving said barrel relative to and within said holder;
    fixedly securing the barrel to the holder;
    applying an adhesive layer to the radially inward facing surface of the barrel at the proximal end of the barrel, and to the radially inward facing surface of the holder at the proximal end of the holder;
    attaching a detector array to the proximal end of the holder; and
    applying vibratory forces to the viewing element to shake loose internal particulate matter particles onto and/or into the adhesive layer.

12. The lens assembly of claim 11, wherein the second diameter is greater than the first and third diameters.

13. The lens assembly of claim 11, wherein said adhesive layer comprises any one or combination of acryl, silicon, a pressure sensitive adhesive, and gel.

14. The lens assembly of claim 11, wherein the first diameter is less than the second diameter.

15. The viewing element of claim 11, wherein said radially outward facing surface of said barrel and said radially inward facing surface of said holder are substantially smooth to allow for movement of said barrel relative to said holder, and for setting said focal length prior to fixedly securing said barrel to said holder.

16. The lens assembly of claim 11 wherein the diameter of the passageway varies by increasing then decreasing as the barrel extends from its proximal end to its distal end.

17. The viewing element of claim 11, wherein a radially inward facing portion of the adhesive layer remains exposed within the passageway and is configured to grab and hold the internal particulate matter particles.

18. The viewing element of claim 11, wherein the diameter of the passageway tapers as the passageway extends along a length of the barrel.

19. A lens assembly manufactured by a process of:

forming a barrel having a length, a proximal end, a distal end, a radially inward facing surface, and a radially outward facing surface;

placing a plurality of lenses into said barrel, wherein a profile of said radially inward facing surface of said barrel is configured to receive and hold said lenses;

sliding said barrel into a holder having a radially inner surface, a proximal end, and a distal end;

setting a focal length by axially moving said barrel relative to and within said holder;

fixedly securing the barrel to the holder; and applying an adhesive layer to a proximal end of the radially innermost surface of the holder, wherein a radially inward facing surface of the adhesive layer remains exposed after fixedly securing the barrel to the holder.

* * * * *